United States Patent
Karamanoglu et al.

(10) Patent No.: US 8,504,158 B2
(45) Date of Patent: Aug. 6, 2013

(54) PHRENIC NERVE STIMULATION DURING CARDIAC REFRACTORY PERIOD

(75) Inventors: Mustafa Karamanoglu, Fridley, MN (US); Vincent E. Splett, Apple Valley, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 13/103,735

(22) Filed: May 9, 2011

(65) Prior Publication Data

US 2012/0290036 A1 Nov. 15, 2012

(51) Int. Cl.
*A61N 1/00* (2006.01)

(52) U.S. Cl.
USPC .......................................................... 607/42

(58) Field of Classification Search
USPC ..................................................... 607/20, 42
See application file for complete search history.

(56) References Cited

U.S. PATENT DOCUMENTS

| | | | |
|---|---|---|---|
| RE30,366 E | 8/1980 | Rasor et al. | |
| 4,721,110 A | 1/1988 | Lampadius | |
| 6,415,183 B1 | 7/2002 | Scheiner et al. | |
| 7,139,607 B1 | 11/2006 | Shelchuk | |
| 7,184,832 B2 * | 2/2007 | Deno et al. | 607/9 |
| 7,277,757 B2 | 10/2007 | Casavant et al. | |
| 7,340,302 B1 * | 3/2008 | Falkenberg et al. | 607/9 |
| 7,392,086 B2 | 6/2008 | Sathaye | |
| 7,596,413 B2 | 9/2009 | Libbus et al. | |
| 7,647,101 B2 | 1/2010 | Libbus et al. | |
| 7,650,189 B1 | 1/2010 | Park et al. | |
| 7,787,946 B2 | 8/2010 | Stahmann et al. | |
| 2005/0065563 A1 | 3/2005 | Scheiner | |
| 2005/0288728 A1 | 12/2005 | Libbus et al. | |
| 2006/0058852 A1 | 3/2006 | Koh et al. | |
| 2006/0149330 A1 | 7/2006 | Mann et al. | |
| 2007/0118183 A1 | 5/2007 | Gelfand et al. | |
| 2008/0097566 A1 | 4/2008 | Colliou | |

FOREIGN PATENT DOCUMENTS

| | | |
|---|---|---|
| EP | 1 634 617 | 3/2006 |
| WO | WO 03/086531 | 10/2003 |
| WO | WO 2006/115774 | 11/2006 |

OTHER PUBLICATIONS

Whittenberger et al., "Electrophrenic Respiration. II. Its use in man," J Clin Invest. Jan. 28, 1949(1): 124-128.
Cigna, "Cigna Healthcare Coverage Position, Subject: Diaphragmatic/Phrenic Nerve Stimulation", (revised date Jul. 15, 2008), pp. 1-5.
(PCT/US2012/036895) PCT Notification of Transmittal of the International Search Report and the Written Opinion of the International Searching Authority.

* cited by examiner

*Primary Examiner* — Christopher D Koharski
*Assistant Examiner* — Philip Edwards
(74) *Attorney, Agent, or Firm* — Reed A. Duthler; Stephen W. Bauer

(57) ABSTRACT

A method includes estimating a cardiac signal of a patient, estimating a length of a cardiac refractory period based in part on the cardiac signal and selectively adjusting the length of phrenic nerve electrical stimulation to be delivered to the patient based on the estimated length of the cardiac refractory period. In some examples the method includes delivering phrenic nerve stimulation for approximately the entire refractory period. The phrenic nerve stimulation may be used to treat a variety of breathing disorders.

28 Claims, 11 Drawing Sheets

PHRENIC NERVE STIMULATION DURING CARDIAC REFRACTORY PERIOD

TECHNICAL FIELD

The disclosure relates to respiratory induction and, more particularly, respiratory inducation by electrical stimulation of one or both of the phrenic nerves.

BACKGROUND

Respiratory induction is helpful in treating a wide range of disordered breathing and respiratory conditions that involve disruption to the normal respiratory cycle. Respiratory induction may be necessary while the patient is asleep or while the patient is awake. However, some of the more common types of disordered breathing occur while the patient is asleep.

Apnea is a relatively common form of disordered breathing characterized by interruptions to a patient's breathing. Often, the interruptions to breathing occur during sleep, at which time the disorder is called sleep apnea. Breathing cessation may occur numerous times during sleep, in some cases hundreds of times a night and for up to a minute or longer. Sleep apnea has multiple classifications based on the source of the dysfunction.

For example, Central sleep apnea (CSA) results from neurological dysfunction, while obstructive sleep apnea (OSA) results form a mechanical blockage of the airway. The mechanical blockage may be due, for example, to fatty neck tissue compressing the trachea. Mixed sleep apnea (MSA) has a combination of mechanical and neurological causes. In addition to sleep apnea, there are other types of disordered breathing including hypopnea (shallow breathing), hypernea (heavy breathing), tachypnea (rapid breathing), dyspnea (labored breathing) and orthopnea (difficulty breathing when lying down). There is a high comorbidity between sleep apnea and congestive heart failure.

Cheyne-Stokes respiration is a specific form of abnormal breathing resulting in apneic intervals. Cheyne-Stokes respiration is characterized by progressively deeper and sometimes faster breathing that is followed by a gradual decrease in tidal volume, resulting in a temporary stoppage in breathing. Hence, Cheyne-Stokes respiration has been described as an oscillation of ventilation between apnea and hypernea.

Various treatments exist for sleep apnea and other disordered breathing including drugs, surgery, and medical device treatments including, for example, using a continuous positive airway pressure (CPAP) machine. The type of treatment depends on the type and severity of the breathing disorder.

SUMMARY

In general, the disclosure is directed to techniques for delivering electrical stimulation to the phrenic nerve or nerves to induce respiration. More specifically, the disclosure is directed to techniques for alleviating disordered breathing through the delivery of phrenic nerve stimulation during the cardiac refractory period in order to deliver stimulation that induces respiration but does not substantially induce cardiac contraction. For patients with congestive heart failure in addition to a breathing disorder, it may be possible to deliver stimulation pulses via an implantable medical device (IMD) to treat both the heart failure and the breathing disorder. In some examples, the temporal length of the phrenic nerve stimulation may be selectively adjusted based on an estimated length of the cardiac refractory period. Also, in some examples, intensity of the phrenic nerve stimulation may be selectively adjusted based on the estimated length of the cardiac refractory period.

In one example, the disclosure is directed to a method including monitoring a cardiac signal of a patient, estimating a length of a cardiac refractory period based at least in part on the cardiac signal, and selectively adjusting a length of phrenic nerve electrical stimulation to be delivered to the patient based at least in part on the estimated length of the cardiac refractory period. In some examples, the method may also include the delivery of the phrenic nerve electrical stimulation during the cardiac refractory period.

In some examples, the method includes monitoring the cardiac signal over a plurality of cardiac cycles. The length of the cardiac refractory period may be updated at a plurality of times based on the cardiac signal over the plurality of cardiac cycles. The length of the phrenic nerve electrical stimulation may be adjusted based on the updated estimated length of the refractory period. For example, the length of the phrenic nerve stimulation may be adjusted based on a first estimated length of the cardiac refractory period, and selectively adjusted one or more times based on the updated estimated length.

In one example, the disclosure is directed to a device including a sensor configured to monitor a cardiac signal of a patient, and a processor configured to estimate a length of a cardiac refractory period based at least in part on the cardiac signal and selectively adjust a length of phrenic nerve electrical stimulation to be delivered to the patient based at least in part on the estimated length of the cardiac refractory period.

The details of one or more examples are set forth in the accompanying drawings and the description below. Other features, objects, and advantages will be apparent from the description and drawings, and from the claims.

DETAILED DESCRIPTION

Figure 1:
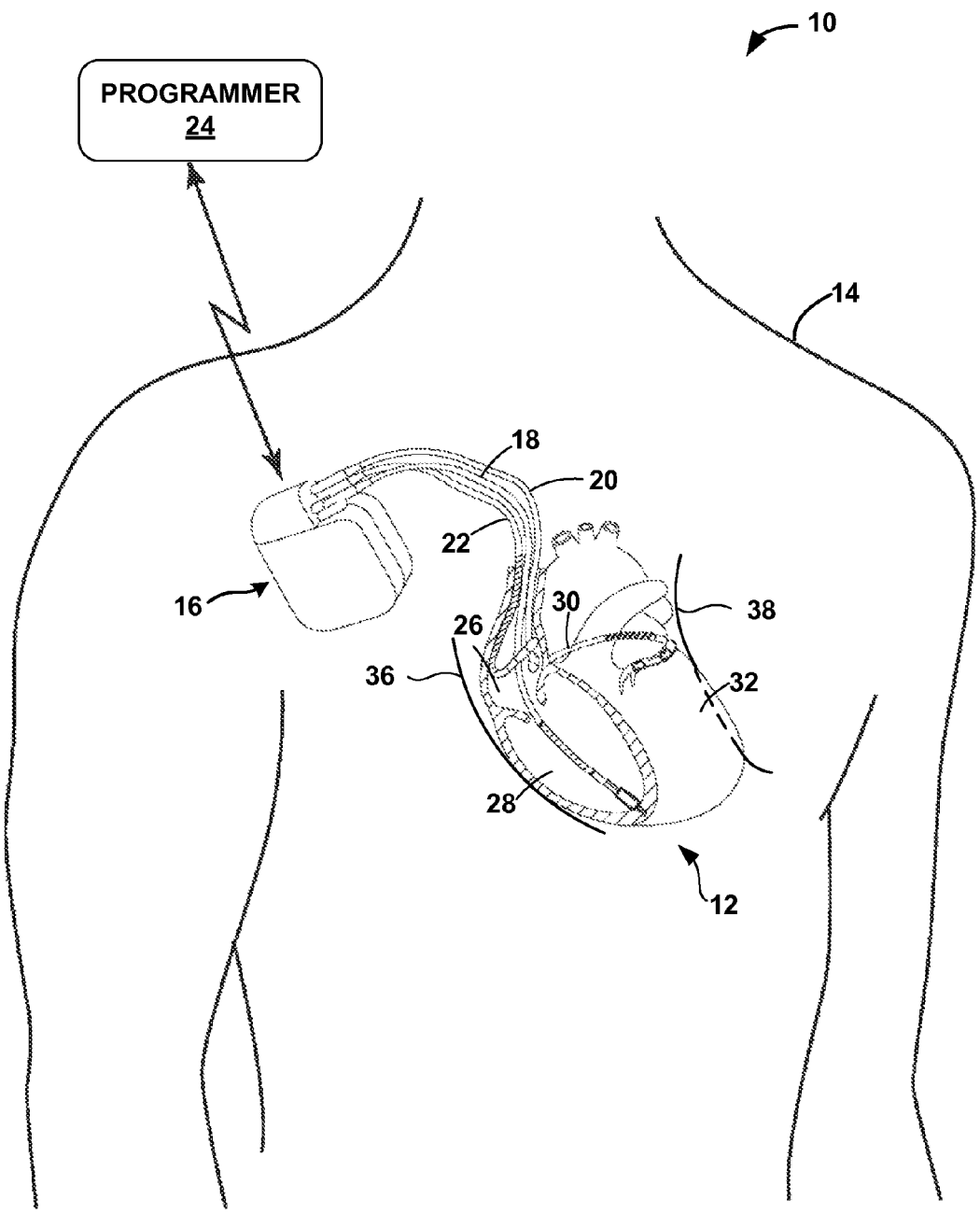
FIG. 1 is a conceptual diagram illustrating an example system that delivers phrenic nerve stimulation, consistent with an example of the present disclosure.

The techniques described in this disclosure may allow a medical device to deliver phrenic nerve electrical stimulation to induce respiration and thereby aid in the treatment of breathing disorders, such as, e.g., breathing disorders that may be associated with cardiac conditions treated by the medical device or by another medical device. The phrenic nerve stimulation may be provided to the left phrenic nerve, the right phrenic nerve or both the left and right phrenic nerves, during the refractory period of the heart muscle, i.e., during the cardiac refractory period.

The temporal length of the phrenic nerve stimulation may be selectively adjusted to provide stimulation based at least in part on an estimated length of the cardiac refractory period. In some examples, given the adjusted length, the timing of delivery of the phrenic nerve stimulation may be selected based on the start of the cardiac refractory period. Also, in some examples, the intensity of the phrenic nerve stimulation may be selectively adjusted based on the estimated length of the cardiac refractory period.

In general, the beginning of a refractory period may be determined based on the application of an electrical stimulation pacing pulse to excite the heart muscle and cause a paced depolarization, in instances where cardiac pacing stimulation is necessary. The refractory period follows an action potential associated with a paced depolarization. Hence, the beginning of the cardiac refractory period may be determined to coincide with the timing of the electrical stimulation pacing pulse, e.g., with the end of the pacing pulse or with the detection of a paced R wave.

In instances where an electrical pacing pulse is not used to trigger depolarization of the cardiac tissue, an electrogram (EGM) signal may be used to determine the beginning of the refractory period, e.g., based on detection of an intrinsic depolarization. In this case, the beginning of the QRS complex, specifically the beginning of the Q-wave in the EGM signal, indicates the beginning of intrinsic depolarization of the heart muscle, and therefore the start of the refractory period.

The end of the cardiac refractory period may not be readily known. However, the cardiac refractory period can be estimated, as will be described. The cardiac refractory period includes two portions, the absolute refractory period and the relative refractory period. The absolute refractory period is the interval from the beginning of the action potential (initiation of depolarization) of the heart muscle until the heart muscle is able to conduct another action potential.

In some examples, the absolute refractory period is approximately 30-40 milliseconds (ms), although the absolute refractory period may vary in length. The relative refractory period follows the absolute refractory period and is the interval in which, despite cardiac cells not being fully recovered, a small action potential may be generated if a sufficiently strong input stimulus is applied. Hence, in the absolute refractory period, an action potential is not possible. In the relative refractory period, an action potential is possible but at least partially inhibited. In some examples, the relative refractory period has a range of approximately 250-400 ms. In general, the transition from the absolute refractory period to the relative refractory period occurs at some time during the T-wave of an EGM signal.

The absolute refractory period is a result of sodium ion channels of the cardiac cells closing. The channels remain closed for a set period of time. While the sodium ion channels are closed, the cell will not respond to further excitation. The duration of the relative refractory period can vary in length. For example, as heart rate increases, and systole decreases, the relative refractory period also decreases. The entire refractory period, both absolute and relative portions, are needed to restore gradient concentrations of ions in the cells and to return the cardiac cells to their resting potential such that the heart muscle is ready for another depolarization.

The refractory period provides a window of opportunity during which stimulation may be supplied to one or both phrenic nerves without causing excitation sufficient to produce a depolarization of the heart. During the absolute refractory period, large electrical stimulations may be applied without causing an action potential. Hence, it is desirable to deliver phrenic nerve stimulation for a period of time selected to be within the refractory period. In some instances, it may be beneficial to apply phrenic nerve stimulation for a period of time longer than the absolute refractory period, e.g., so as to provide increased stimulation of respiration. However, as the relative refractory period progresses, the amount of stimulation that may be applied without triggering a depolarizing event diminishes.

Therefore, it may be desirable to deliver phrenic nerve stimulation for a period of time that spans portions of the absolute refractory period and the relative refractory period, but which is selected to avoid triggering significant cardiac stimulation during the relative refractory period. In these cases, it may be beneficial to determine when the refractory period transitions to a point in time in the relative refractory period, i.e., an excitation point, at which there is a risk that a depolarization may be triggered by phrenic nerve stimulation. In particular, it may be beneficial to determine at what point during the relative refractory period the intensity of the electrical pulse being used to stimulate the phrenic nerve could result in excitation of the cardiac cells near the electrode providing stimulation. This excitation may not correspond to a depolarization but may indicate a risk of depolarization if the stimulation is applied later in the relative refractory period.

In accordance with various examples of this disclosure, phrenic nerve stimulation may have a length and/or intensity that is selected based on an estimated length of the refractory period. As one example, the phrenic nerve stimulation may be selected to have a length substantially equal to an estimated period of time between the start of the absolute refractory period and a time in the relative refractory period at which the phrenic nerve stimulation may cause cardiac excitation. As another example, the phrenic nerve stimulation may have a length substantially equal to the above estimated length of time, minus a first margin of time after the start of the absolute refractory period and before the start of the phrenic nerve stimulation, and/or minus a second margin of time after the end of the phrenic nerve stimulation and before the onset of cardiac excitation. These lengths and margins of time may be used to select the length and timing of the phrenic nerve stimulation relative to a cardiac refractory period.

In some examples, the estimated length of the refractory period may be a period from the detected or paced start of the refractory period to a point that is a predetermined time interval later in time than the start of the absolute refractory period. The predetermined time interval may be determined based on an expected time between the start of the refractory period and a point in time at which phrenic nerve stimulation is expected to cause cardiac excitation, e.g., based on expected periods of time or heart rate for a given patient or population of patients. Alternatively, the estimated length of the refractory period may be a period between a detected R-wave and a detected T-wave. As a further alternative, the estimated length of the refractory period may be a period between the detected or paced start of the refractory period and a point in time selected based on detection of cardiac excitation in response to one or more electrical probing pulses or bursts, as will be described. For example, one or more probing pulses or bursts, which may be referred to generally as probing stimulation, may be delivered to the patient at an intensity selected for detection of the onset of cardiac excitation, i.e., the excitation point, to thereby detect a point in the relative refractory period at which the relative refractory period may be approach its end, and at which phrenic nerve stimulation could cause undesirable cardiac excitation.

The start of the absolute refractory period and the excitation point in the relative refractory period may be detected in one or more cardiac cycles and then used as the basis to select the length and timing of delivery of phrenic nerve stimulation in later cardiac cycles. In some examples, the intensity of phrenic nerve stimulation may be selectively adjusted during the refractory period to reduce a risk of triggering nearby cardiac cells, while still providing electrical stimulation sufficient to maintain activation of the phrenic nerve and cause substantial respiratory activity. For example, during a first margin of time at the start of phrenic nerve stimulation and/or a second margin of time at the end of phrenic nerve stimulation, the phrenic nerve stimulation may be turned off or have a reduced intensity, relative to the therapeutic intensity selected for the remaining duration of the phrenic nerve stimulation. The intensity may be a function of current or voltage amplitude, pulse width and/or pulse rate of the stimulation.

As an example, the phrenic nerve stimulation may be turned off in a first margin of time between the detected start of the refractory period and a later time at which phrenic nerve stimulation is commenced, or the intensity of the phrenic nerve stimulation can be increased from a first level to a second level, in a step-wise manner or gradually over time, in the first margin of time. As a further alternative, the phrenic nerve stimulation can be turned off during the first margin of time, and then upon commencement of phrenic nerve stimulation, the intensity can be increased step-wise or gradually.

Similarly, the phrenic nerve stimulation may be turned off for a second margin of time after delivery of phrenic nerve stimulation but before the end of the estimated length of the refractory period, or step-wise or gradually reduced in intensity during the second margin of time, or turned off during the second margin of time and reduced in intensity up to the time the stimulation is turned off. The first and second margins of time may be fixed or variable, or specified by a clinician or other user, and the timing of the phrenic nerve stimulation may be determined based on estimated length of time of the refractory period, as obtained by monitoring previous cardiac cycles.

The intensity of the stimulation may be modulated to provide various levels of phrenic nerve stimulation, which in turn may result in the diaphragm being activated at various rates or to varying degrees. The modulation may occur within a refractory period, as described above, or across multiple refractory periods. For example, the intensity of phrenic nerve stimulation may be increased or reduced during a refractory period of a given cardiac cycle, e.g., in the first and/or second margins of time discussed above. Alternatively or additionally, as one example, a lower stimulation intensities may be provided in the refractory periods of one or more cardiac cycles, and higher stimulation intensities may be provided in the refractory periods of one or more other cardiac cycles, thereby adjusting the degree of stimulation over a series of cycles to induce respiration by the patient in a controlled manner.

In summary, phrenic nerve stimulation may be delivered for a length of time that is selected based at least in part on an estimated length of the refractory period, such as a fixed period of time from the detected start of the refractory period in one or more previous cardiac cycles, a period of time between an R wave and a T wave for one or more previous cardiac cycles, or a period of time between the detected start of the refractory period and a point in time corresponding to an expected excitation point, e.g., based on a detected excitation point in the relative refractory period of one or more previous cardiac cycles. Hence, in some examples, the length and timing of phrenic nerve stimulation may be selected to reside within a portion of a refractory period prior to an excitation point. In some cases, the intensity of the phrenic nerve stimulation, e.g., by way of amplitude, pulse width, and/or pulse rate, may vary within a given cardiac cycle and/or among successive cardiac cycles, to provide effective respiratory induction therapy while avoiding substantial cardiac stimulation.

FIG. 1 is a conceptual diagram illustrating an example system 10 that may provide both phrenic nerve stimulation and cardiac tissue stimulation to a patient 14. In particular, system 10 may monitor both cardiac and respiratory-based signals and provides stimulation based on a set of parameters. One or more of the stimulation parameters may be chosen in response to information collected from the monitored signals. In some examples, the respiratory-based signals may be used to determine whether the patient 14 has a breathing disorder, such as sleep apnea, that may be treated through phrenic nerve stimulation. The determination of a breathing disorder may also rely on other information such as the detected cardiac signals, for example. In other examples, the system 10 detects the occurrence of a disorder episode and applies stimulation in response to the detection. The disorder episode may be breathing disorder or a cardiac disorder. For example, the patient 14 may stop breathing for a period of time. Alternatively, the heart may be exhibiting signs of arrhythmia. The system 10 may determine what kind of disorder is present, and provide therapeutic stimulation (cardiac, respiratory, or both) chosen based on the disorder(s) present.

System 10 includes implantable medical device (IMD) 16, which is connected to leads 18, 20 and 22 and is optionally communicatively coupled to programmer 24. IMD 16 senses electrical signals attendant to the depolarization and repolarization of heart 12, e.g., a cardiac EGM, via electrodes on one or more leads 18, 20 and 22 or the housing of IMD 16. In some examples, IMD 16 also delivers cardiac therapy in the form of electrical signals to heart 12 via electrodes located on one or more leads 18, 20 and 22 or a housing of IMD 16. The cardiac therapy may be pacing, cardioversion and/or defibrillation pulses. The IMD 16 may also provide respiratory induction therapy. The respiratory induction therapy may include delivery of electrical stimulation to one or both phrenic nerves 36 and 38 via electrodes located on one or more leads 18, 20 and 22 or a housing of IMD 16. In some examples, the electrodes used to stimulate phrenic nerves 36 and 38 may be used for both cardiac and phrenic nerve stimulation. The electrodes may also be used to sense either cardiac or respiratory-based signals. In other examples, IMD 16 also may include one or more respiratory sensors (not shown in FIG. 1) used to detect the breathing patterns of patient 14. IMD may similarly include or be coupled to other sensors, such as one or more accelerometers, for detecting other physiological parameters of patent 14, such as activity or posture.

In some examples, programmer 24 may take the form of a handheld computing device, computer workstation or networked computing device that includes a user interface for presenting information to and receiving input from a user. A user, such as a physician, technician, surgeon, electro-physiologist, or other clinician, may interact with programmer 24 to retrieve physiological or diagnostic information from IMD 16. A user may also interact with programmer 24 to program IMD 16, e.g., select values for operational parameters of the IMD. In certain examples various functions of the programmer 24 may be automated. For example, the operational parameters may be selected automatically in response to one or more cardiac metrics. In other examples, the programming functions of programmer 24 may be split between external programmer and IMD 16. For example, IMD 16 may be configured to automatically select or adjust one or more parameters of the cardiac or phrenic nerve stimulation, e.g., based on monitored cardiac or respiratory signals.

IMD 16 and programmer 24 may communicate via wireless communication using any techniques known in the art. Examples of communication techniques may include, for example, low frequency or radiofrequency (RF) telemetry. Other techniques are also contemplated. In some examples, programmer 24 may include a programming head that may be placed proximate to the patient's body near the IMD 16 implant site in order to improve the quality or security of communication between IMD 16 and programmer 24. In other examples, programmer 24 may be located remotely from IMD 16, and communicate with IMD 16 via a network.

Leads 18, 20, 22 extend into the heart 12 of patient 14 to sense electrical activity of heart 12 and/or deliver electrical stimulation to heart 12. The leads may also deliver electrical stimulation to phrenic nerve 38. In the example shown in FIG. 1, right ventricular (RV) lead 18 extends through one or more veins (not shown), the superior vena cava (not shown), and right atrium 26, and into right ventricle 28. Left ventricular (LV) coronary sinus lead 20 extends through one or more veins, the vena cava, right atrium 26, and into the coronary sinus 30 to a region adjacent to the free wall of left ventricle 32 of heart 12. Right atrial (RA) lead 22 extends through one or more veins and the vena cava, and into the right atrium 26 of heart 12. In some examples, RA lead 22 may be used to stimulate right phrenic nerve 36. In other examples, LV coronary sinus lead 20 may be used to stimulate left phrenic nerve 38.

Techniques for stimulating one or more of phrenic nerves 36 and 38 are primarily described herein as being performed by IMD 16, e.g., by a processor of IMD 16. In other examples, some or all of the analytical, processing and control functions ascribed to IMD 16 or a processor thereof may be performed by one or more other devices such as programmer 24, or a processor thereof. For example, IMD 16 may process cardiac and/or respiratory-based signals to determine whether cardiac stimulation therapy and/or phrenic nerve stimulation therapy (collectively "therapy") should continue to be delivered based on current parameters, or whether adjustments to the parameters should be made, and control the parameters used by IMD 16 to deliver the therapy. Alternatively, programmer 24 may process cardiac and/or respiratory-based signals received from IMD 16 to determine whether therapy should continue to be delivered based on current parameters or whether adjustments to the parameters should be made, and control under what parameters IMD 16 delivers the therapy. Furthermore, although described herein with respect to an IMD, in other examples, the techniques described herein may be performed or implemented in an external medical device, which may be coupled to a patient via percutaneous or transcutaneous leads. In other examples, various functions of IMD 16 may be carried out by multiple IMDs in communication with one another.

Figure 2:
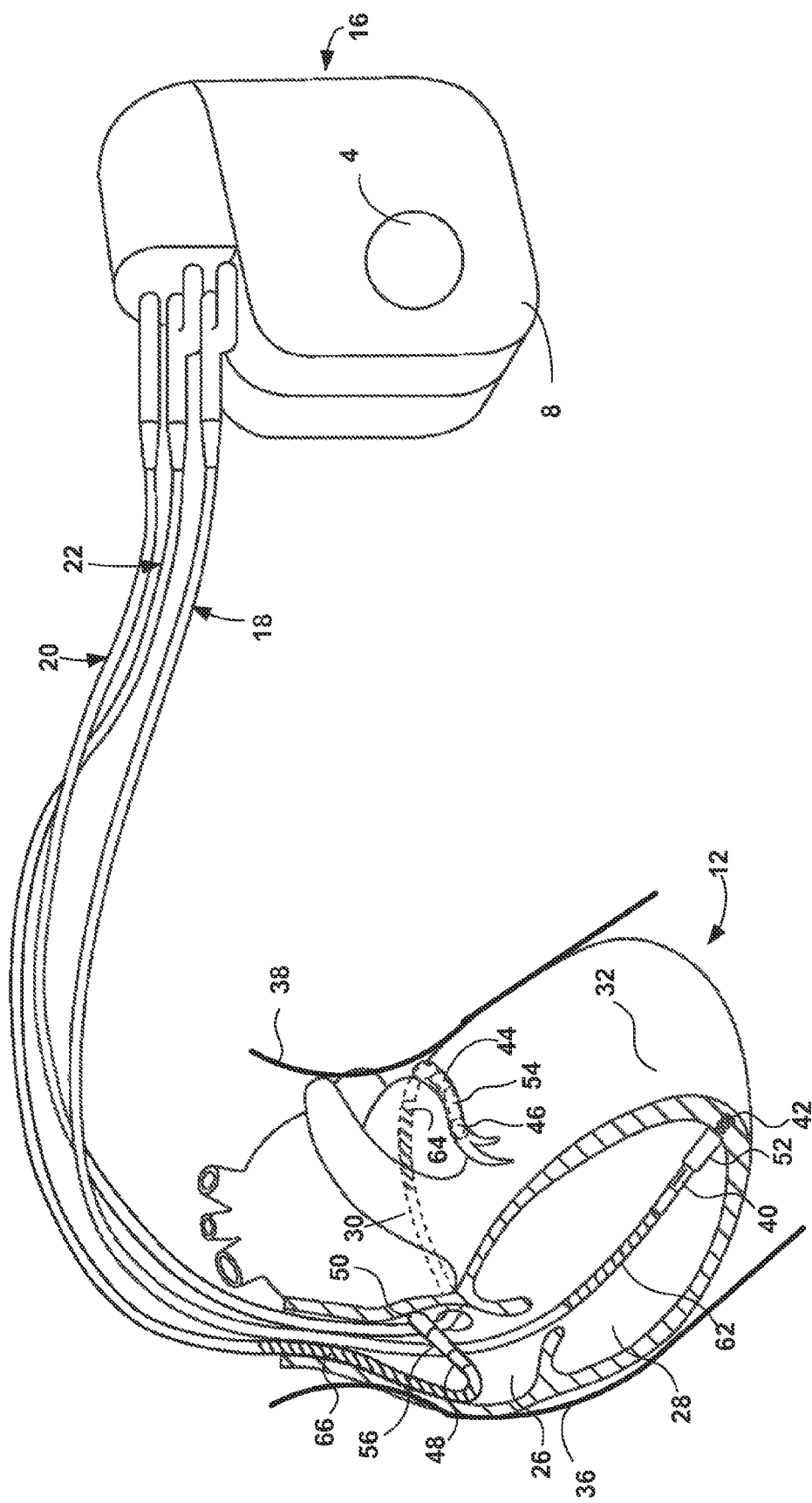
FIG. 2 is a conceptual diagram illustrating the implantable medical device (IMD) and leads of the system shown in FIG. 1 in greater detail.

FIG. 2 is a conceptual diagram illustrating IMD 16 and leads 18, 20 and 22 of system 10 in greater detail. In the illustrated example, bipolar electrodes 40 and 42 are located adjacent to a distal end of lead 18. In addition, bipolar electrodes 44 and 46 are located adjacent to a distal end of lead 20, and bipolar electrodes 48 and 50 are located adjacent to a distal end of lead 22. In alternative examples, not shown in FIG. 2, one or more of leads 18, 20 and 22 may include quadrapole electrodes located adjacent to a distal end of the lead.

In the illustrated example, electrodes 40, 44 and 48 take the form of ring electrodes, and electrodes 42, 46 and 50 may take the form of extendable helix tip electrodes mounted retractably within insulative electrode heads 52, 54 and 56, respectively. Leads 18, 20, 22 also include elongated electrodes 62, 64, 66, respectively, which may take the form of a coil. In some examples, each of electrodes, 40, 42, 44, 46, 48, 50, 62, 64 and 66 is electrically coupled to a respective conductor within the lead body if its associated lead 18, 20, 22 and thereby coupled to circuitry within IMD 16.

In some examples, IMD 16 includes one or more housing electrodes, such as housing electrode 4 illustrated in FIG. 2, which may be formed integrally with an outer surface of hermetically-sealed housing 8 of IMD 16 or otherwise coupled to housing 8. In some examples, housing electrode 4 is defined by an uninsulated portion of an outward facing portion of housing 8 of IMD 16. Other divisions between insulated and uninsulated portions of housing 8 may be employed to define two or more housing electrodes. In some examples, a housing electrode comprises substantially all of housing 8.

As described in further detail with reference to FIG. 3, housing 8 encloses a signal generator that generates therapeutic stimulation, such as cardiac pacing, cardioversion and defibrillation pulses, as well as a sensing module for sensing electrical signals attendant to the depolarization and repolarization of heart 12. IMD 16 may also include a respiratory sensor that monitors the patient's breathing. The respiratory sensor may be, for example an accelerometer, a microphone, transthoracic impedance, EMG of the diaphragm, air flow sensor, acoustical sensor, oxygen sensor, strain gauge or other sensors. The respiratory sensor may be enclosed within housing 8. Alternatively, the respiratory sensor may be integrally formed with or carried on an outer surface of housing 8, carried on or within a lead coupled to IMD 16, such as one or more leads 18, 20 and 22, or be a separate, remote sensor that wirelessly communicates with IMD 16, programmer 24 or any other device describe herein.

IMD 16 senses electrical signals attendant to the depolarization and repolarization of heart 12 via unipolar or bipolar combinations of electrodes 4, 40, 42, 44, 45, 48, 50, 62, 64 and 66. IMD 16 may sense such electrical signals via any bipolar combination of electrodes 40, 42, 44, 46, 48, 50, 62, 64 and 66. Furthermore, any of the electrodes 40, 42, 44, 46, 48, 50, 62, 64 and 66 may be used for unipolar sensing in combination with housing electrode 4. In some examples, the electrodes may sense respiratory-based signals. For example, one or more electrodes may detect electrical signals associated with the activation of the phrenic nerve(s).

Figure 4:
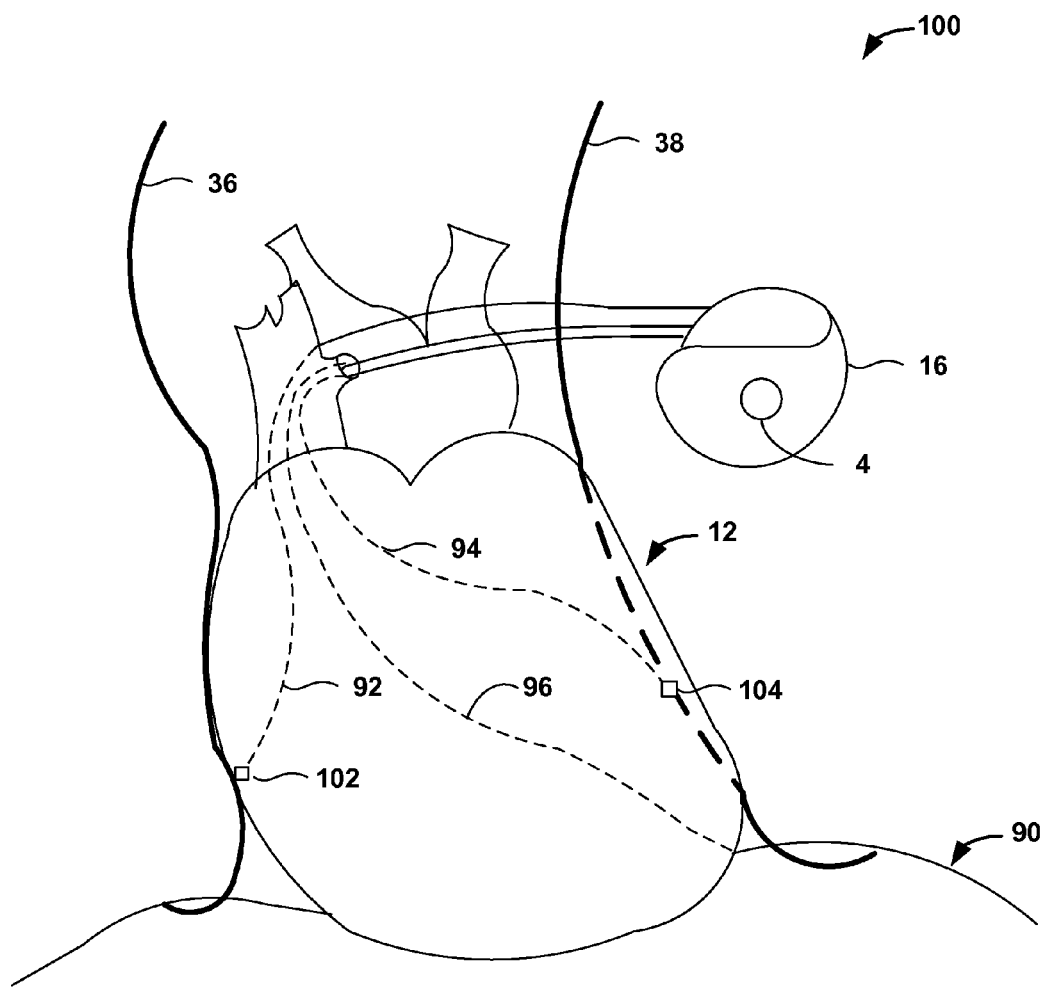
FIG. 4 is a conceptual diagram illustrating an example system that delivers phrenic nerve stimulation.

In some examples, IMD 16 delivers stimulation pulses via bipolar combinations chosen based on EGM signals and/or respiratory signals as analyzed by a signal analyzer within IMD. For example, bipolar combinations of electrodes 40, 42, 44, 46, 48, and 50 are used to produce depolarization of cardiac tissue of heart 12. In addition, phrenic nerve stimulation pulses may be delivered by various electrodes chosen based on the location of the electrodes used to provide cardiac stimulation. In some examples, IMD 16 delivers stimulation to either cardiac tissue or the phrenic nerve(s) via any of electrodes 40, 42, 44, 46, 48 and 50 in combination with housing electrode 4 in a unipolar configuration. In some examples, left phrenic nerve 38 is stimulated, right phrenic nerve 36 may be stimulated, or both phrenic nerves may be stimulated. As shown in FIG. 4, below, one or more of the leads of IMD 16 may be placed in order to provide stimulating pulses to one or both of phrenic nerves 36 and 38. In other examples, the choice of electrodes delivering cardiac and phrenic nerve electrical stimulation may be based on default settings. Furthermore, IMD may deliver cardioversion or defibrillation pulses to heart 12 or phrenic nerves 36 and 38 via any combination of elongated electrodes 62, 64, 66 and housing electrode 4.

The illustrated numbers and configurations of leads 18, 20 and 22 and electrodes are merely examples. Other configurations, i.e., number and position of leads and electrodes, are possible. In some examples, system 10 may include an additional lead or lead segment having one or more electrodes positioned at different locations in the cardiovascular system for sensing and/or delivering therapy to patient 14. For example, instead of or in addition to intracardiac leads 12, 20 and 22, system 10 may include one or more epicardial or subcutaneous leads not positioned within the heart. For example, a lead may be positioned to provide one or more electrodes in contact with phrenic nerve 36 or phrenic nerve 38. As another example, system 10 may include an additional lead that carries a respiratory sensor positioned such that signals generated by the respiratory sensor include information regarding a patient's respiratory activity including, for example, inspiration and expiration.

Figure 3:
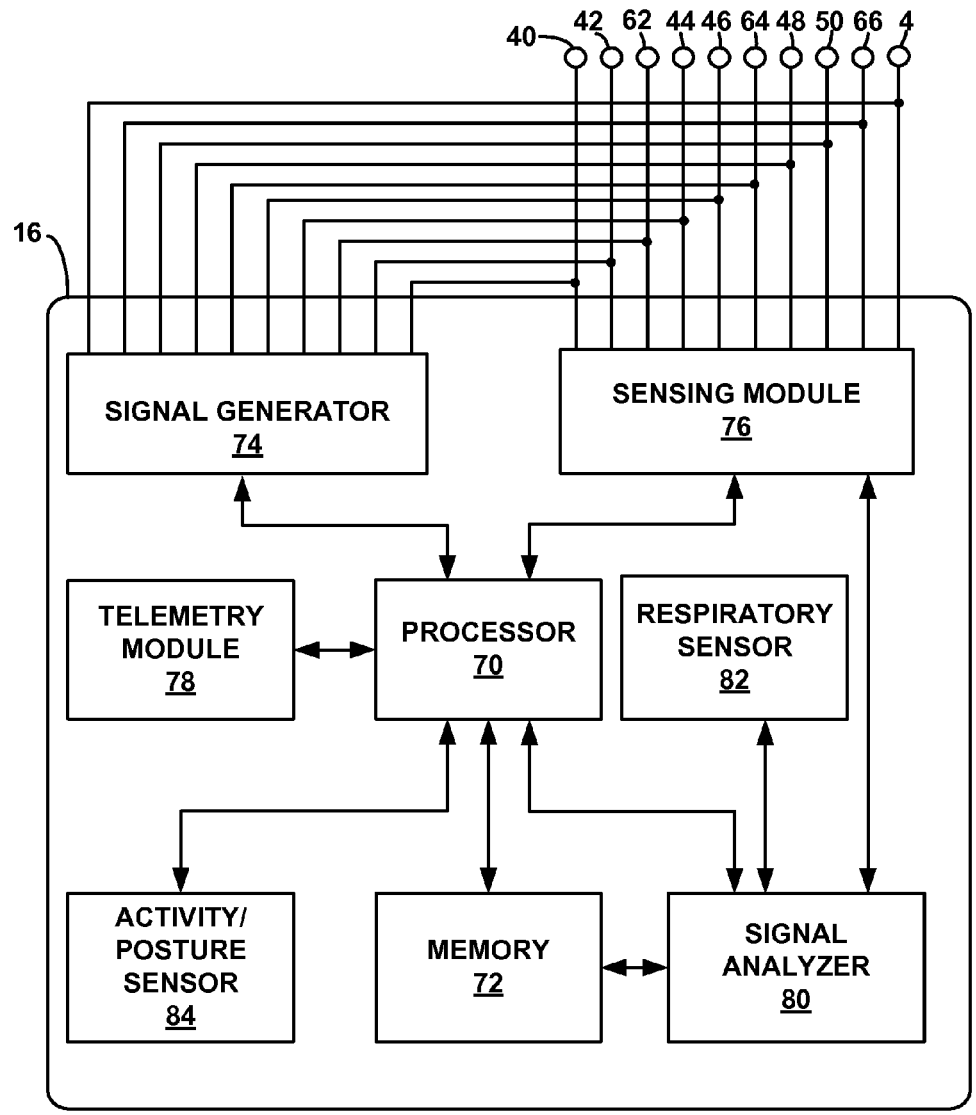
FIG. 3 is a block diagram illustrating an example configuration of the IMD of FIG. 1.

FIG. 3 is a block diagram illustrating an example configuration of IMD 16. In the illustrated example, IMD 16 includes a processor 70, memory 72, signal generator 74, sensing module 76, telemetry module 78, a signal analyzer 80, a respiratory sensor 82, and an activity/posture sensor 84. Memory 72 includes computer-readable instructions that, when executed by processor 70, cause IMD 16 and processor 70 to perform various functions attributed to IMD 16 and processor 70 herein. Memory 72 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media.

Processor 70 may include any one or more of a microprocessor, a controller, a digital signal processor (DSP), an application specific integrated circuit (ASIC), a field-programmable gate array (FPGA), or equivalent discrete or analog logic circuitry. In some examples, processor 70 may include multiple components, such as any combination of one or more microprocessors, one or more controllers, one or more DSPs, one or more ASICs, or one or more FPGAs, as well as other discrete or integrated logic circuitry. The functions attributed to processor 70 herein may be embodied as software, firmware, hardware or any combination thereof. Generally, processor 70 controls signal generator 74 to deliver stimulation therapy to heart 12 of patient 14 according to a selected one or more of therapy programs or parameters, which may be stored in memory 72. As an example, processor 70 may control signal generator 74 to deliver electrical stimulation pulses with the amplitudes, pulse widths, frequency, or electrode polarities specified by the selected one or more therapy programs. The stimulation pulses may include cardiac stimulation pulses and phrenic nerve stimulation pulses. The therapy programs may be selected by the programmer 70 based on information from the signal analyzer 80.

Signal generator 74 is configured to generate and deliver electrical stimulation therapy to patient 12. For example, signal generator 74 may be configured to selectively generate electrical stimulation for cardiac pacing, cardioversion-defibrillation or phrenic nerve stimulation. Alternatively, separate signal generators may be provided in IMD 16 to deliver cardiac stimulation and phrenic nerve stimulation, respectively. A single signal generator 74 that may be configured to selectively deliver cardiac stimulation or phrenic nerve stimulation will be described for purposes of illustration. As shown in FIG. 3, signal generator 74 is electrically coupled to electrodes 4, 40, 42, 44, 46, 48, 50, 62, 64 and 66, e.g., via conductors of the respective leads 18, 20, and 22 and, in the case of housing electrode 4, within housing 8. For example, signal generator 74 may deliver stimulating pulses to phrenic nerves 36 and 38 via at least two of electrodes 4, 40, 42, 44, 46, 48, 50, 62, 64 and 66, e.g., in bipolar or unipolar combinations. In addition, in some examples, signal generator 74 may deliver pacing pulses, defibrillation shocks or cardioversion shocks to heart 12 via at least two of electrodes 4, 40, 42, 44, 46, 48, 50, 62, 64 and 66. In other examples, signal generator 74 delivers stimulation in the form of waveforms other than pulses such as sine waves, square waves, or other substantially continuous time signals.

Signal generator 74 may include a switch module (not shown) and processor 70 may use the switch module to select, e.g., via a data/address bus, which of the available electrodes are used to deliver the electrical stimulation. The switch module may include a switch array, switch matrix, multiplexer, or any other type of switching device suitable to selectively couple stimulation energy to selected electrodes. Electrical sensing module 76 monitors electrical cardiac signals from any combination of electrodes 4, 40, 42, 44, 46 48, 50, 62, 64, and 66. Sensing module 76 may also include a switch module which processor 70 controls to select which of the available electrodes are used to sense the heart activity, depending upon which electrode combination is used in the current sensing configuration. In some examples, a separate signal generator may be provided for each electrode such that a switch module is not necessary.

Sensing module 76 may include one or more detection channels, each of which may comprise an amplifier. The detection channels may be used to sense the cardiac signals. Some detection channels may detect events, such as R-waves, T-waves, or P-waves, and provide indications of the occurrences of such events to processor 70 and/or signal analyzer 80. One or more other detection channels may provide the signals to an analog-to-digital converter, for conversion into a digital signal for processing or analysis by processor 70 or signal analyzer 80.

For example, sensing module 76 may comprise one or more narrow band channels, each of which may include a narrow band filtered sense-amplifier that compares the detected signal to a threshold. If the filtered and amplified signal is greater than the threshold, the narrow band channel indicates that a certain electrical cardiac event, e.g., depolarization, has occurred. Processor 70 then uses that detection in measuring frequencies of the sensed events. Signal analyzer 80 may use the detection in connection with sensed heart sounds to determine one or more cardiac metrics.

In one example, at least one narrow band channel may include an R-wave or P-wave amplifier. In some examples, the R-wave and P-wave amplifiers may take the form of an automatic gain controlled amplifier that provides an adjustable sensing threshold as a function of the measured R-wave or P-wave amplitude. Examples of R-wave and P-wave amplifiers are described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety.

In some examples, sensing module 76 includes a wide band channel which may comprise an amplifier with ah relatively wider pass band than the narrow band channels. Signals from the electrodes that are selected for coupling to the wide-band amplifier may be converted to multi-bit digital signals by an analog-to-digital converter (ADC) provided by, for example, sensing module 76, processor 70, or signal analyzer 80. Processor 70 may analyze the digitized version of signals from the wide band channel. Processor 70 may employ digital signal analysis techniques to characterize the digitized signals from the wide band channel to, for example, detect and classify the patient's heart rhythm. In other examples, the signal analyzer 80 employs digital signal analysis techniques to characterize the digitized signals from the wide band channel. The digitized signals may be used in conjunction with respiratory-based signals to determine when, and if, a phrenic nerve stimulating electrical pulse should be applied.

Processor 70 may detect and classify a patient's breathing disorder based on respiratory based signals sensed by respiratory sensor 82 and/or cardiac electrical signals detected by sensing module 76, employing any of the numerous signal processing methodologies known in the art. In certain examples, processor 70 may provide the processed signal to signal analyzer 80 for further processing or combination with respiratory-based signals. In other examples, sensing module 76 provides at least some of the cardiac electrical signals directly to signal analyzer 80. In still other examples, sensing module 76 provides the senses cardiac electrical signals to both processor 70 and signal analyzer 80 for different signal processing.

In various examples, processor 70 may maintain escape interval counters that may reset upon sensing of R-waves by sensing modules 76. The value of the count present in the escape interval counters when reset by sensed depolarizations may be used by processor 70 to measure the durations of R-R intervals, which are measurement that may be stored in memory 72 and may be used by signal analyzer 80. Processor 70 may use the count in the interval counters to detect a tachyarrhythmia, such as ventricular fibrillation or ventricular tachycardia. A portion of memory 72 may be configured as a plurality of recirculating buffers, capable of holding a series of measured intervals, which may be analyzed by processor 70 to determine whether the patient's heart 12 is presently exhibiting atrial or ventricular tachyarrhythmia.

In the example in FIG. 3, e.g., to aid in the treatment of breathing disorders, IMD 16 also includes respiratory sensor 82 and signal analyzer 80. Respiratory sensor 82 generates electrical signals based on sensed respiratory behavior. In some examples, the respiratory sensor 82 may comprise more than one sensor. For example, the respiratory sensor 82 may include multiple individual sensors. In some examples, the respiratory sensor 82 may include one or more electrodes monitoring at least one of phrenic nerves 36 and 38. In other examples, the respiratory sensor 82 is an acoustic sensor such as an accelerometer, microphone or piezolectric device. The acoustic sensor picks up sounds resulting from the activation of the diaphragm.

In the illustrated example of FIG. 3, respiratory sensor 82 is enclosed within housing 8 of IMD 16. In some examples, respiratory sensor 82 may be formed integrally with or on an outer surface of housing 8. In other examples, respiratory sensor 82 is located on one or more leads that are coupled to IMD 16 or may be implemented in a remote sensor that wirelessly communicates with IMD 16. In any case, respiratory sensor 82 is electrically or wirelessly coupled to circuitry contained within housing 8 of IMD 16.

Signal analyzer 80 receives the electrical signal generated by respiratory sensor 82. In one example, signal analyzer 80 may process the sensor signal generated by respiratory sensor 82 to detect occurrences of inspiration. In some examples, the signal analyzer 80 may classify the detected occurrences of inspiration. In other examples, signal analyzer 80 processes the respiratory sensor signal to generate an envelope signal, detects occurrences of inspiration using a threshold, and extracts respiration features from the detected respiratory signal. The respiratory features may include length of inspiration, frequency of inspiration, and depth of inspiration, for example. In some examples, the detected respiratory features may be compared to threshold values for each feature stored in memory 72. The respiratory features may then be classified based on deviation from the stored values. The respiratory features and/or their classifications may be used to determine whether respiration if normal or represents an episode of disordered breathing such that phrenic nerve stimulation should be applied to induce respiration.

In some examples, the classified respiratory features are used by the signal analyzer along with EGM information extracted from an EGM signal collected by the sensing module 76. In some examples, the EGM information may be extracted by the sensing module 76 and provided to processor 70. The EGM information may then be provided to the signal analyzer 80 from memory 72 or processor 70. In some examples, some or all of the signal processing attributed to signal analyzer 80 may be performed by processor 70, such that the functionality of signal analyzer 80 may be functionality of processor 70, e.g., programmable functionality in some cases. In some examples, the unprocessed signal is provided to processor 70 by sensing module 76 for information extraction. In other examples, the EGM information may also be extracted from the EGM signal by the signal analyzer 80. Examples of the operation of signal analyzer 80 and processor 70 in accordance with these example methods are described in greater detail with respect to FIGS. 5-7. A respiratory-based indication may be output from signal analyzer 80 to processor 70. In other examples, the respiratory features may be output to processor 70 for analysis. Processor 70 may initiate phrenic nerve stimulation based on the information received from signal analyzer 80. Processor 70 may also stop or adjust ongoing phrenic nerve stimulation based on the information received.

Signal analyzer 80 may be configured to detect the start of the refractory period, e.g., based on a timing of paced depolarization or detection of a paced or intrinsic depolarization. In addition, in some examples, signal analyzer 80 may be configured to detect an excitation point in the refractory period, i.e., a point in time at which stimulation, e.g., stimulation at an intensity approximately equal to that of the phrenic nerve stimulation, causes cardiac excitation, such as a threshold degree of cardiac excitation. As will be described, following detection of the start of the refractory period in some cardiac cycles, processor 70 may direct signal generator 74 to deliver one or more short probing pulses or bursts that may have an intensity, e.g., in amplitude, pulse rate and/or pulse width, selected to detect cardiac activation suggesting progression of the relative refractory period toward the end of the refractory period.

A probing burst may include one or more pulses, which may have an amplitude, pulse width and/or pulse rate selected to elicit cardiac activation in the relative refractory period. In some examples, the pulse has an amplitude of approximately 1 to 10V and a pulse width within the range of approximately 0.1-1.5 ms. In some examples, the probing pulses have an amplitude of approximately 2.5 to 5 V and a pulse width of approximately 0.5 to 1 ms. In some examples, the probing pulses are delivered at a frequency of between 10-100 Hz. In other examples there is a single probing pulse. If probing stimulation causes cardiac excitation, processor 70 may identify the point at time that the probing stimulation was delivered as the excitation point for the refractory period. The excitation point may be used by processor 70, either alone or in combination with other detected excitation points for other cardiac cycles, to select the length of the phrenic nerve stimulation, based on the period between the start time of the refractory period and the time of the excitation point, which period may serve as an estimated length of the refractory period.

FIG. 4 is a conceptual diagram illustrating an example system 100 for applying phrenic nerve stimulation. The system 100 includes an IMD 16 that monitors respiratory based signals and provides phrenic nerve stimulation based on a set of parameters chosen in response to information collected from the monitored signal. In some examples, IMD 16 may also monitor cardiac-based signals, e.g., EGM signals, and may also provide cardiac tissue stimulation. In some examples, the detected respiratory-based signals are used to determine whether the patient has a breathing disorder, such as sleep apnea, that may be treated through phrenic nerve stimulation. In other examples, the system 100 detects the occurrence of a disorder episode and applies phrenic nerve stimulation in response. The disorder episode may be a breathing disorder or a cardiac disorder. In each case, for example, the patient may stop breathing for a period of time. Alternatively, the heart may be exhibiting signs of arrhythmia. The system 100 may determine what kind of disorder is present, and provide therapeutic stimulation (cardiac stimulation or phrenic nerve stimulation) chosen based on the disorder present.

System 100 includes an IMD 16, which is connected to leads 92, 94, and 96, and is optionally communicatively coupled to a programmer (not shown in FIG. 4). IMD 16 may be configured to sense various signals attendant to the activation of diaphragm 90 in response to electrical stimulation to phrenic nerves 36 and 38. In some examples, the signals are detected with electrodes 102 and 104 of leads 92 and 94, respectively. IMD 16 may also provide respiratory induction therapy. The respiratory induction therapy includes electrical stimulation delivered to one or more of phrenic nerves 36 and 38 via electrodes 102 and 104, respectively. In some examples, lead 92 is arranged so that electrode 102 is in the coronary sinus of heart 12. In some examples, electrode 102 may be located in in the right ventricle or the inferior vena cava.

In some examples electrodes 102 and 104 are unipolar electrodes and provide stimulation in connection with electrode 4 on IMD 16. In some examples, electrodes 102 and 104 are bipolar electrodes, each of electrodes 102 and 104 providing stimulation in connection with another electrode on a lead, not shown. The additional electrodes may be located on one or more of leads 92, 94 and 96. In some examples, IMD 16 also senses electrical signals attendant to the depolarization and repolarization of heart 12, e.g., a cardiac EGM, via electrodes on one or more of leads 92, 94, and 96, or the housing of IMD 16. In some examples, IMD 16 may deliver cardiac therapy in the form of electrical signals to heart 12 via electrodes located on one or more of leads 92, 94, and 96 to IMD 16. In some examples, lead 96 may be positioned so that one or more electrodes on lead 96 may be used to deliver cardiac therapy. IMD 16 may also include or be coupled to other sensors, such as one or more accelerometers for detecting other physiological parameters of a patient, such as activity of posture.

Techniques for stimulating one or more of right phrenic nerve 36 or left phrenic nerve 38 are primarily described herein as being performed by IMD 16, e.g., by a processor of IMD 16. For example, IMD 16 may process respiratory-based signals to determine whether the IMD 16 should continue to deliver phrenic nerve stimulation based on current parameters, or whether adjustments to the parameters should be made. The processor in IMD 16 may also control the parameters used by IMD 16 to deliver therapy.

Figure 5:
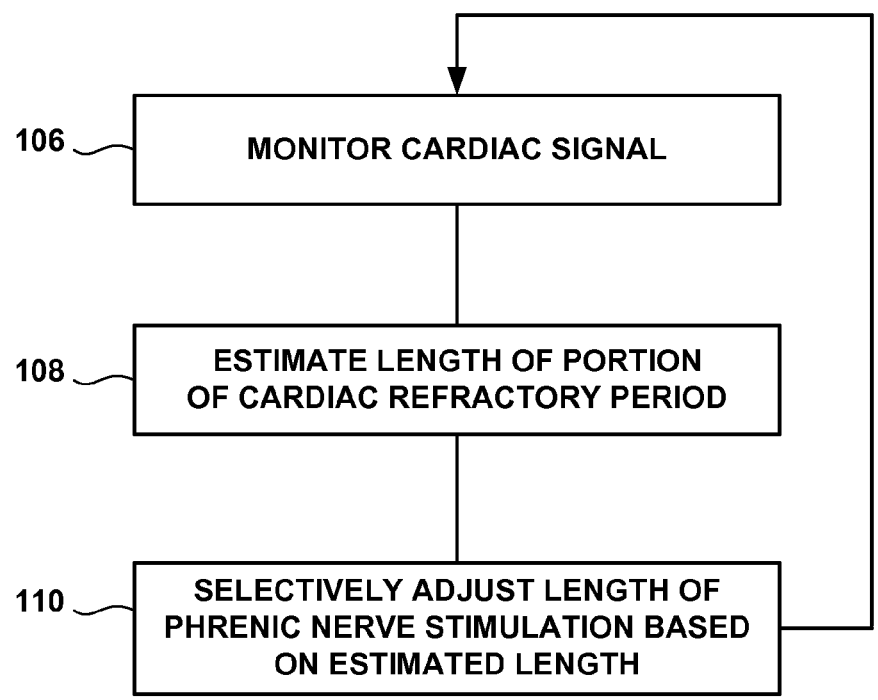
FIG. 5 is a flow diagram illustrating an example mode of operation for delivering phrenic nerve stimulation, consistent with an example of the present disclosure.

FIG. 5 is a flow chart illustrating an example mode of operation for delivering phrenic nerve stimulation, consistent with various examples of the present disclosure. Various examples include an IMD that provides electrical stimulation to a patient's phrenic nerve on a controlled basis in order to induce inspiration. In many examples, the stimulation may support therapy for a chronic breathing disorder. In other examples, phrenic nerve stimulation is provided in response to an acute episode of respiratory dysfunction. In various examples, the phrenic nerves stimulation is provided during the refractory period of the patient's heart.

As discussed above, the length of the refractory period, including the absolute refractory period and relative refractory period, may change. IMD 16 monitors a cardiac signal (106) of a patient. In some examples, the signal is an EGM signal obtained by sensing module 76 and analyzed by signal analyzer 80. IMD 16 estimates the length of the cardiac refractory period (108) based at least in part on the cardiac signal. The estimated length may be a length of time extending from the detected start of the refractory period, e.g., as detected by a paced or intrinsic depolarization, and a later point in time. The later point in time may be a time that follows the start of the refractory period of time by a predetermined interval. The predetermined interval may correspond to an interval of time that is expected to be within the refractory period and, in some cases, between the start of the refractory period and the excitation point, e.g., based on data for a particular patient or patient population. In some examples, the length of the refractory period is estimated based upon a patient's heart rate. In some examples, the estimation of the length of the cardiac refractory period may be based on the length of time between the R-wave and the T-wave of the EGM signal. As a further alternative, the estimated length may be a length of time extending from the detected start of the refractory period to a detected excitation point, e.g., a point at which stimulation by a probing pulse or burst produces detectable cardiac excitation.

If an excitation point is determined, the estimation may be based on the length of time between the application of an electrical stimulation pacing pulse resulting in a cardiac action potential and the application of a second (probing) pulse that results in a small, localized action potential. In some examples, the intensity of the probing stimulation may be greater than or equal to the intensity of the phrenic nerve stimulation, e.g., in current or voltage pulse amplitude, pulse width or pulse rate, but the duration of the probing pulse or burst may be substantially shorter than the duration of the phrenic nerve stimulation. In some cases, the duration of the probing pulse or burst may be insufficient to cause significant induction of respiration In some examples, the estimation of the length of the cardiac refractory period is based on the estimation of the length of the cardiac refractory period over a plurality of heart beats, i.e., cardiac cycles. For example, the estimation of length may be based on an average of the determined lengths of time between the start of the refractory period and the excitation point for each cardiac cycle since the last application of phrenic nerve stimulation. In some examples, the estimated of length may be updated at a plurality of times based on changes in an average detected length over multiple cardiac cycles. The length of phrenic nerve stimulation is selectively adjusted (110) based on the estimated length of the refractory period. In some examples, the adjustment may be made before each application of the electrical stimulation to the phrenic nerve if there has been a change to the estimated length of the refractory period. In some examples, an adjustment is made in response to an updated estimate of the length of the portion of the refractory period. In other examples, adjustments are made when a change in the estimated length of the refractory period is larger than a predetermined amount.

In some examples, the phrenic nerve stimulation may not be applied during each refractory period. Instead, the frequency of application may be based on a desired breathing rate. As discussed above, the respiration rate is slower than the heart rate. For example, for a patient who has a heart rate of 60 beats per minute, the phrenic nerve stimulation may be applied every sixth refractory period to provide a breathing rate of 10 breaths per minute. In other examples, a series of electrical stimulation waveforms may be applied in two or more successive refractory periods. The use of more than one stimulation waveform may allow for inspiration lasting closer to the length of a normal inspiration. The number of phrenic nerve stimulation waveforms during subsequent refractory periods used may be determined based on the breathing disorder being treated. In various examples, the frequency of the phrenic nerve stimulation may be modified based on the desired breathing rate and the current heart beat rate for a given patient. In some examples, the respiratory response to the phrenic nerve stimulation pulses may also be sensed. If the pulses are insufficient to produce a respiratory response, the amplitude, pulse width or pulse rate may be altered so that a respiratory response is produced.

Figure 6:
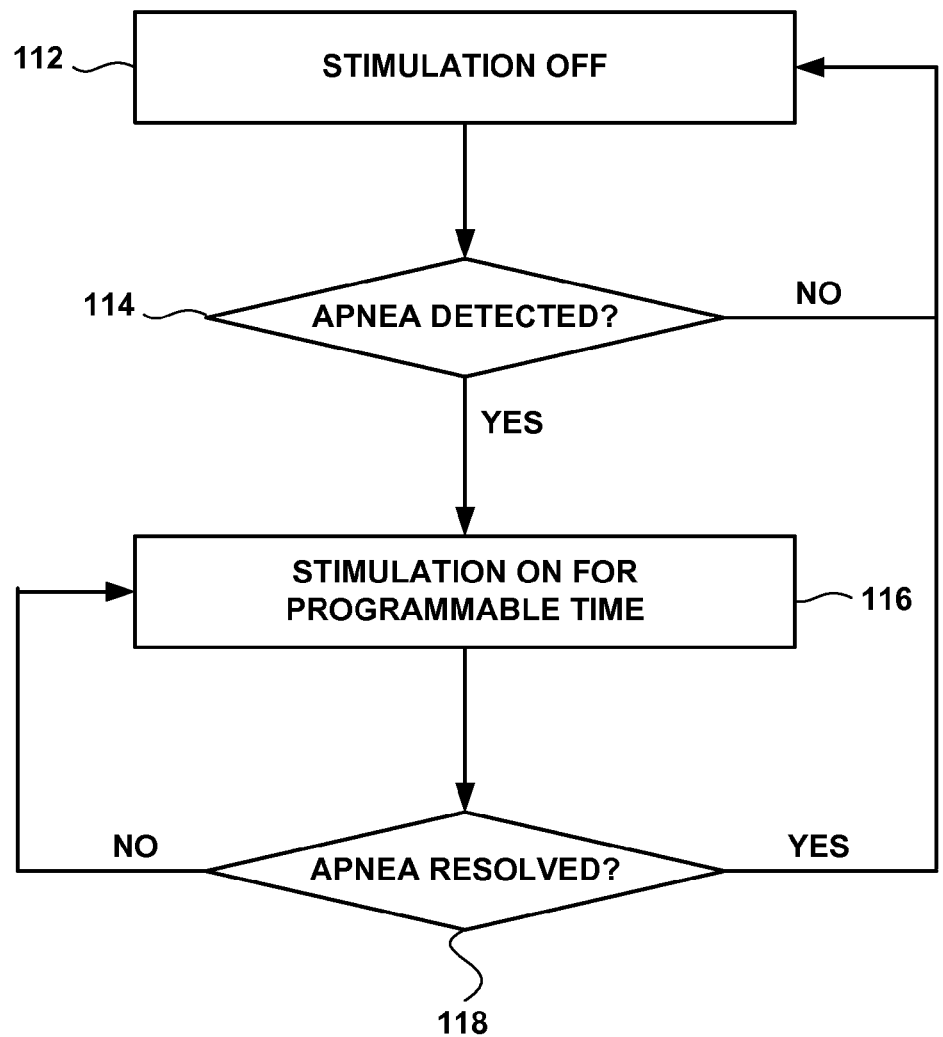
FIG. 6 is a flow diagram illustrating an example method of treating apnea using phrenic nerve stimulation consistent with an example of the present disclosure.

FIG. 6 is a flow chart illustrating an example mode of operation for delivering phrenic nerve stimulation to treat an episode of apnea. When no apnea has been detected, the phrenic nerve stimulation is off (112). In some examples, IMD 16 may be applying cardiac pacing stimulation while the phrenic nerve stimulation is off. In various examples, the IMD 16 monitors respiratory-based signals using respiratory sensor 82 and EGM signals using sensing module 76. Signal analyzer 82 is used to detect the presence of apnea (114), e.g., based on signals from sensing module 76 and/or respiratory sensor 82. If no apnea is detected, the phrenic nerve stimulation continues to be off. If an apnea is detected, then stimulation is turned on for a programmable time (116). In some examples, the programmable time includes a plurality of refractory periods, during each of which stimulation may be applied. In some examples, processor 70 initiates stimulation based on the detection of apnea. In some examples, phrenic nerve stimulation only occurs during one or more cardiac refractory periods within the programmable time. The length of the phrenic nerve stimulation may be based on the estimated length of the refractory period. In some examples, the phrenic nerve stimulation has a length substantially equal to an estimated length of the refractory period. In certain examples, the relationship between the length of the refractory period and the length of the stimulation provided is chosen based on the type of apnea detected or the number of times stimulation has been provided. After application of the phrenic nerve stimulation, signal analyzer 82 determines whether the apnea has been resolved (118). Resolution of apnea may include the return to a breathing pattern with a range of normal or acceptable breathing patterns. For example, one or more phrenic nerves may be activated without stimulation from IMD 16. If the apnea has not been resolved, then a subsequent stimulation pulse may be provided to the phrenic nerve. In some examples, the subsequent stimulation may occur in the next refractory period. In other examples, the subsequent stimulation may be applied after an interval based on a desired breathing pattern. The stimulation continues to be applied during the refractory period until the respiratory sensor 80 and the signal analyzer 82 determine that breathing has returned to within a normal range with the aid of phrenic nerve stimulation. This determination may be based at least in part on the detection of electrical activity in the phrenic nerve not associated with the application of a stimulating waveform by IMD 16.

Using sleep apnea as an example, apnea may be detected (114) based on the absence of inspiration over a predetermined period of time. In some examples, the absence may be detected using a respiratory sensor 82, which may be an accelerometer or other sensor that picks up motion or sounds. In other examples, respiratory sensor 82 may include an electrical sensor may be placed near one or more of the phrenic nerves and the absence of an electrical pulse over the phrenic nerve for a predetermined amount of time may result in a determination of apnea. Phrenic nerve stimulation may be provided to phrenic nerves 36 and 38 at a rate consistent with an expected breathing rate such as, for example, 10 breaths per minute. The phrenic nerve stimulation takes over for the missing native breathing for a given period of time. The amount of time may be determined based on the type of apnea detected or on data regarding previous apnea episodes for the patient. After the stimulation has been on for the programmable time (116), IMD 16 may monitor signals from the phrenic nerves 36 and 38 or sounds from the activation of diaphragm 90 over a period of time to determine if the apnea has resolved and whether independent breathing has been restored. If so, stimulation is turned off (112).

Figure 7:
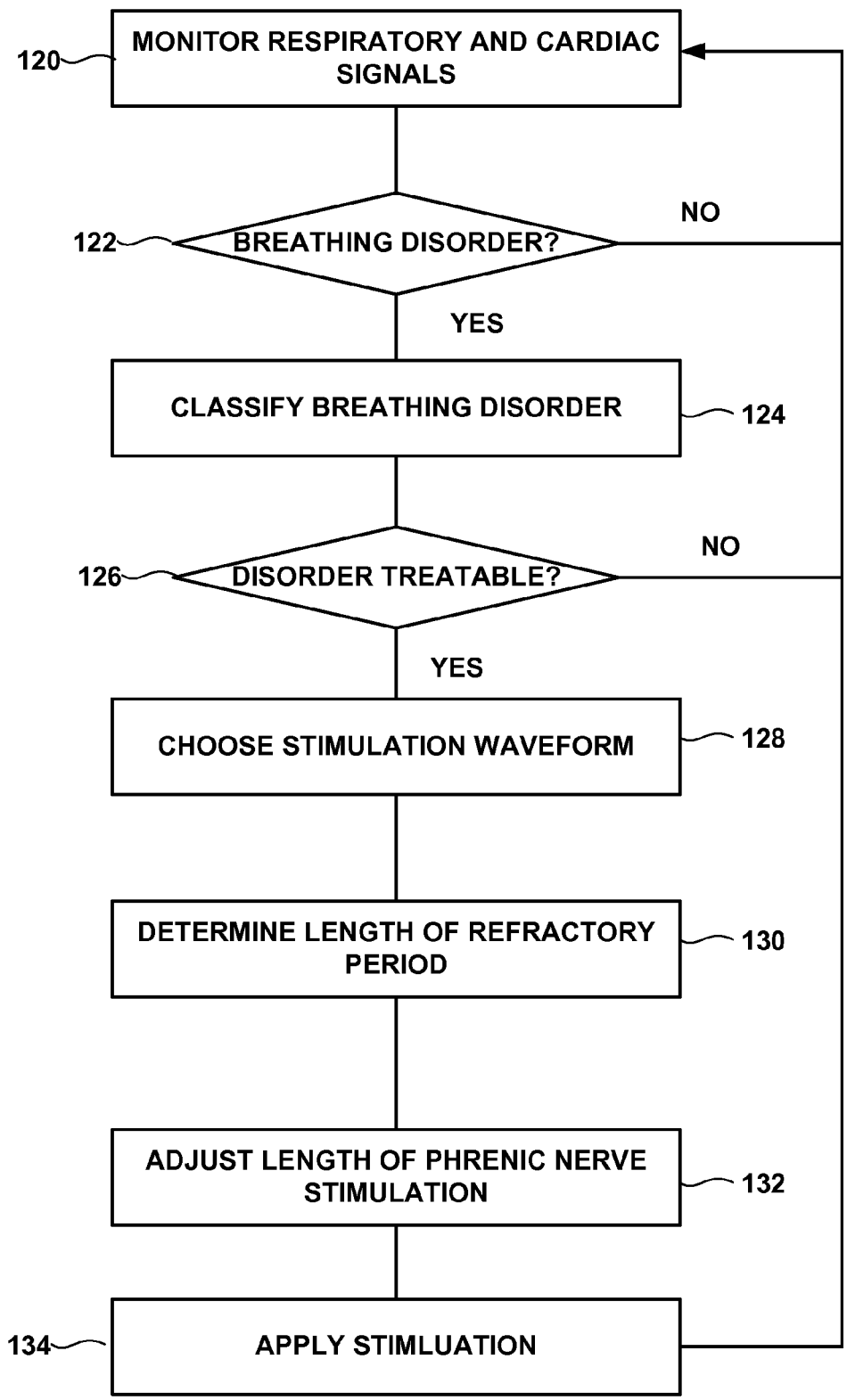
FIG. 7 is a flow diagram illustrating an example method of delivering phrenic nerve stimulation.

FIG. 7 is a flow diagram illustrating an example method of delivering phrenic nerve stimulation. IMD 16 monitors respiratory signals using respiratory sensor 82 and monitors cardiac signals using sensing module 76 (120). The respiratory sensor 82 provides the respiratory signal to signal analyzer 80. The signal analyzer 80 determines if the patient has an episode of a breathing disorder (122). If there is no breathing disorder present, IMD 16 continues to monitory respiratory and cardiac signals. In some examples, the IMD 16 may continue to apply cardiac pacing therapy. If the signal analyzer 80 determines that a breathing order exists, the signal analyzer 80 may classify the breathing disorder (124). In some examples, the classification may be based on type of disorder. For example, the classification may indicate whether the patient has stopped breathing (apnea), whether the patient has shallow breathing (hypopnea), or whether the patient is breathing rapidly (tachypnea).

The signal analyzer 80 may determine if the detected classified breathing disorder is treatable using phrenic nerve stimulation (126), i.e., the type of disorder if appropriate for delivery of phrenic nerve stimulation. In some instances, it may appear that the disorder may resolve itself without intervention. In other instances, the disorder may rise to a level of disordered breathing warranting phrenic nerve stimulation treatment. For example, a single missed breath may not result in phrenic nerve stimulation. If the disorder is not treatable, the IMD 16 continues to monitor respiratory and cardiac signals (120). In some examples, telemetry module 78 may transmit an indication of the presence of a non-treatable breathing disorder to an external device such as programmer 24. In other examples, the IMD 16 may store information regarding the untreated disorder in memory 72 for later interrogation. For example, if a single missed breath becomes a pattern, IMD 16 may begin to treat breathing abnormalities not normally treated. In other instances, the information may be stored for collection by a physician when the patient 12 comes in for a check up.

If the disorder is treatable with phrenic nerve stimulation, processor 70 may choose a stimulation waveform (128) for treatment of the breathing disorder based on the classification of the breathing disorder. In some examples, the choice of stimulation waveform (128) may also be based on information from memory 72. For example, processor 70 may reference a lookup table of breathing disorders stored in memory 72 to determine the appropriate stimulation waveform. In other examples, the choice of waveform (128) may be based in part on information from an EGM signal. For example, a different waveform may be chosen if the heart rate is above a certain threshold. This may be the case because the length of the relative refractory period is shortened at higher heart rates, and the shorter refractory period may result in the slope of the change of stimulus level needed to activate the cardiac cells during the refractory period becoming steeper. In other examples, the shortened overall refractory period may make stimulation intensity modulation within a given waveform impractical. In some examples, the shorter refractory period during a higher heart rate may result in the phrenic nerve stimulation being applied over a greater number of successive cardiac refractory periods to ensure adequate length of inspiration.

Next, IMD 16 may determine the length of the cardiac refractory period (130). In some examples, processor 70 uses information stored in memory 72 regarding the temporal length of one or more of the previous refractory periods to estimate the length of the next refractory period. The estimated refractory period length may be determined based on the EGM signal, for example. Processor 70 or signal analyzer 80 may estimate the refractory period as a period from a detected or paced start of the refractory period to a point that is a predetermined time interval later in time than the start of the absolute refractory period. The predetermined time interval may be determined based on an expected time between the start of the refractory period and a point in time at which phrenic nerve stimulation is expected to cause cardiac excitation, e.g., based on expected periods of time for a given patient or population of patients.

Alternatively, the estimated length of the refractory period may be a period between a detected R-wave and a detected T-wave. As a further alternative, the estimated length of at least a portion of the refractory period may be a period between the detected or paced start of the refractory period and a point in time selected based on detection of cardiac excitation in response to one or more electrical probing pulses or bursts. The use of probing stimulation is discussed in more detail with respect to FIG. 8.

As further shown in FIG. 7, IMD 16 adjusts the length of the phrenic nerve stimulation waveform based on the estimated length of the refractory period (132). In some examples, the adjustment includes lengthening or shortening the phrenic nerve stimulation waveform by adding pulses to or removing pulses from the end of the waveform. In other examples, the adjustment includes expanding or shrinking the length of the waveform in proportion to the change in phrenic nerve stimulation from a standard or default length for which the waveform is configured. In some examples, the length of the phrenic nerve stimulation may be approximately equal to the estimated length of the cardiac refractory period. In other examples, the length of the phrenic nerve stimulation delivered to the patient may be approximately equal to the estimated length of the refractory period minus a predetermined time margin before and/or after the phrenic nerve stimulation. The time margin (or safety margin) may be 5% of the estimated length of the refractory period, for example. In some examples, the time margin before the beginning of stimulation may be different than the time margin between the end of stimulation and the end of the estimated refractory period.

IMD 16 then applies phrenic nerve stimulation (134) having the adjusted waveform to patient. The phrenic nerve stimulation may be applied to one or both of phrenic nerves 36 and 38. In some examples, PNS is delivered after detection of an R-wave. In some examples, PNS is delivered after a pacing pulse as has been delivered by IMD 16. In certain examples, the stimulation is applied via preselected electrodes. In some examples, the PND is delivered to follow a detected expiration. This may allow the PNS to synchronize with native breathing. For example, in some instances the patient 14 may need help inhaling to an adequate level. In other examples, the choice of electrodes may be dependent on the choice of stimulation waveform. After application of the stimulation (134), IMD 16 continues to monitor both respiratory and cardiac signals (120). Processor 70 may control the timing of the phrenic nerve stimulation based on the estimated length of the refractory period and based on the start of the refractory period. For example, processor 70 may detect the start of a current refractory period, e.g., based on detection of a paced or intrinsic depolarization, and immediately apply the phrenic nerve stimulation from the detected depolarization for a length of time corresponding to the estimated length of the refractory period, where the estimated length is determined from past cardiac cycles. As discussed above, the estimated length of the refractory period may be determined using a predetermined interval of time which may be adjusted according to heart rate, a detected R-T wave interval for one or more past cardiac cycles, or a detected time between a start of a refractory period and a detected excitation point over one or more past cardiac cycles. For a predetermined interval, detected R-T interval or detected excitation time, the length may be estimated over a plurality of cardiac cycles, e.g., as an average, such that the estimated length of the refractory period is updated over time. For a predetermined interval, the length may be adjusted over time based on R-T or R-R interval or other sensed heart rate parameters. In this case, the predetermined interval may be adjusted to have different values as a function of heart rate. If the R-T or R-R interval decreases, for example, the predetermined interval selected as an expected refractory period length may be decreased, e.g., in a manner proportional to the R-T or R-R interval, or some other measure of heart rate.

Figure 8:
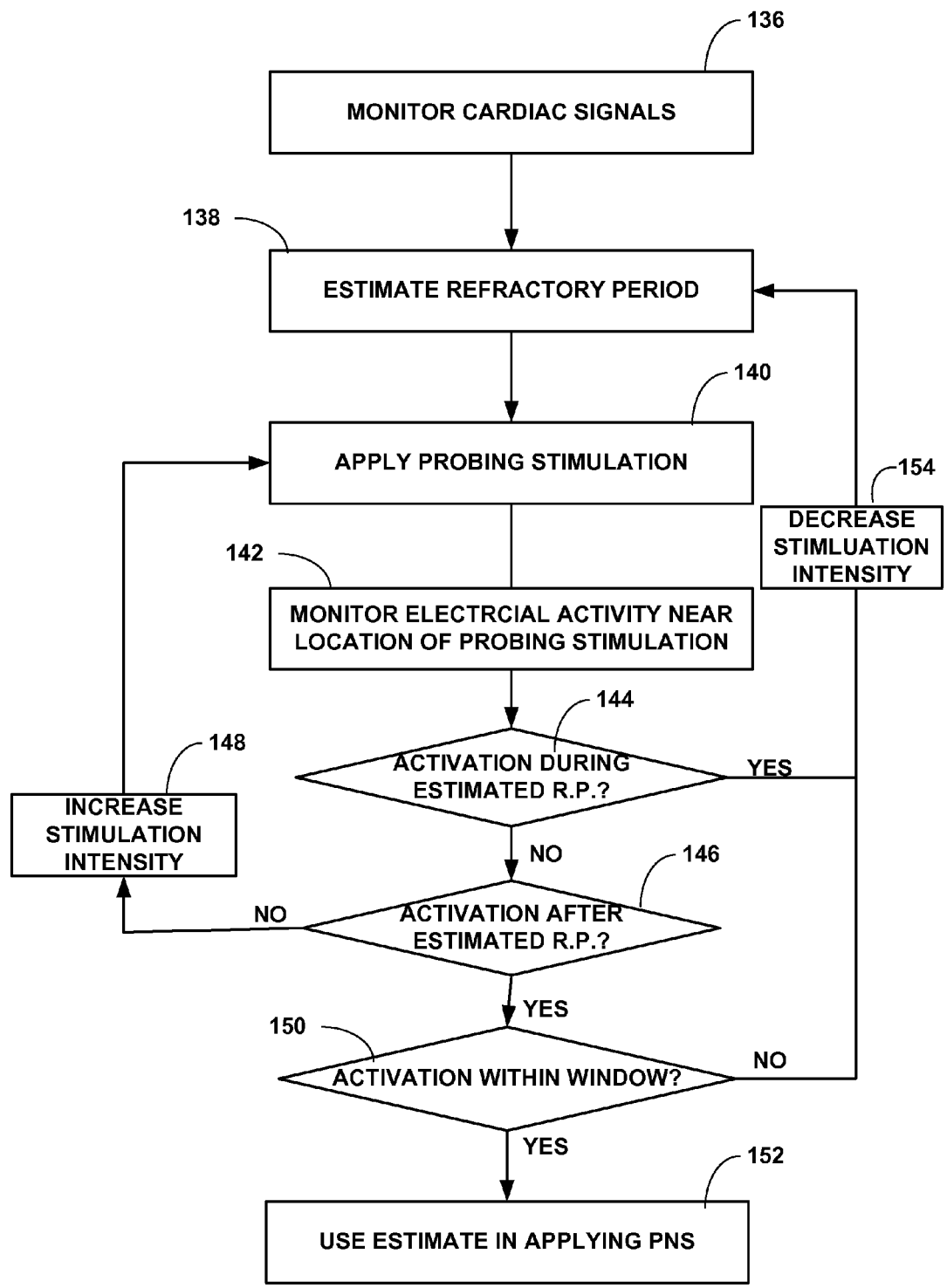
FIG. 8 is a flow diagram illustrating an example method of determining the length of a cardiac refractory period in more detail.

FIG. 8 illustrates a flow diagram of an example method for estimating the length of the cardiac refractory period based on the time between the detected start of the refractory period and a detected excitation point. The IMD 16 monitors cardiac signals (136). In some examples, the cardiac signal is an EGM signal. The IMD 16 makes an initial estimate of the refractory period (138). The estimate may be based on the time between the beginning of the Q-wave and middle of the T-wave from the monitored EGM signal.

IMD 16 then applies probing pulses or bursts of pulses (140), referred to as probing stimulation, to a preselected area of cardiac tissue. In some examples, the probing pulses are applied at a low level of intensity in order to elicit an electrical response but not a full action potential near the end of the relative refractory period. In some examples, the probing stimulation is applied at the same level of intensity as the phrenic nerve stimulation. In various examples, the probing pulses are applied starting after depolarization of the cardiac tissue being studied through the estimated cardiac refractory period, and for an additional amount of time after the estimated start of cardiac refractory period. In some examples, the probing pulses are provided for substantially the entire Q to Q interval. In other examples, the probing pulses start after the R-wave and last until the subsequent Q-wave. The probing pulses may be delivered at a predetermined frequency, for example between 10-100 Hz, until activation is detected or until the beginning of the next refractory period, for example. In some examples, the pulses are applied by a single electrode in a unipolar arrangement. For example, the probing pulses may be applied by one of electrodes 44 or 46. In some examples, the probing pulses are provided to the electrodes by signal generator 74.

In some examples, the probing pulses may have an amplitude of approximately 2.5 to 5V. In some examples, the pulse width is approximately 0.5 to 1 ms. In some examples, the probing pulses consist of a single pulse applied at approximately the end of the estimated cardiac refractory period.

IMD 16 monitors electrical activity near the location of the probing pulse (142). In some examples, electrodes near the electrode used to apply the probing pulses are used to monitor for an electrical response to the probing pulses or bursts. In other examples, the electrode that delivers the probing pulses also is used to monitor the surrounding area for an electrical response to the probing pulses. In some examples, sensing module 76 receives signals from the one or more electrodes monitoring the cardiac tissue for a response to the electrical stimulation probing pulses.

The IMD 16 determines, based on the collected electrical signals, whether any cardiac excitation occurred during the estimated refractory period (144) in response to the probing pulses or bursts. The determination may be focused on whether activation occurred in the area surrounding the electrode that applied the probing pulses, for example. In some examples, the activation in response to the applied probing pulse is less than a full activation of the action potential. If there was activation during the cardiac refractory period, then IMD 16 calculates a new estimated refractory period (138) based on the timing of the delivery of the probing pulse or bursts that caused excitation. This time at which the probing pulse or burst was delivered may be referred to as the excitation time.

The length of the refractory period then may be estimated as a time between the start of the refractory period, e.g., as determined by pacing time or detection of paced or intrinsic depolarization, and the time at which the probing pulse or burst that caused the activation was delivered.

In some examples, the probing simulation intensity may be decreased (154). In instances where the estimate of the length of the refractory period includes both the absolute and relative refractory periods, an initial stimulation intensity equal to initial phrenic nerve stimulation intensity may result in excitation before the end of the relative refractory period. Information regarding the timing of excitation at the phrenic nerve stimulation intensity may be stored in memory 72, for example. IMD 16 may then decrease probing stimulation intensity (154) for application of probing stimulation during a subsequent refractory period. This may allow for both the determination of the slope of the change in the stimulation intensity needed to excite the cardiac tissue during the relative refractory period, and, over a plurality of refractory periods, provide an estimate of when the relative refractory period ends. In some examples, the timing of an early activation may indicate that the initial estimate may be off by more than a predetermined threshold, for example. This determination may be made based on information stored in memory 72 regarding time until activation during previous refractory periods with probing stimulation of the same intensity. In some examples, the next series of probing pulses may be for the same estimated refractory period or for a shortened refractory period.

In some examples, if the activation occurs within a predetermined window surrounding the estimated refractory period length, then IMD 16 ends the refractory period estimation protocol and uses the currently estimated length of the refractory period in applying phrenic nerve stimulation (152). If there is no activation during the refractory period, then IMD 16 determines, in some examples, if there was activation after the refractory period (146). If there was no activation before or after the end of the estimated refractory period, then IMD 16 may increase the stimulation intensity (148) of the probing stimulation to be applied by signal generator 74.

IMD 16 then applies probing stimulation (140) in the next cardiac cycle using the newly altered stimulation intensity. If there is activation after the estimated refractory period, then IMD determines whether the activation was within a window (150) of acceptable deviation from the currently estimated length of the refractory period. If the activation occurred outside of the time window, then IMD 16 may modify the refractory period length estimate (138) and again applies probing stimulation (140). In some examples, both the estimated length of refractory period and the stimulation intensity may be changed. In other examples, only one or the other is changed before the subsequent application of probing stimulation. If the activation occurred during the window surrounding the estimated cardiac refractory period, then IMD 16 uses the estimate in apply subsequent phrenic nerve stimulation (150). In some examples, the estimate used in applying subsequent phrenic nerve stimulation is an updated estimate resulting from information collected from probing stimulation applied over a plurality of refractory periods.

In some examples, if the activation is within the predetermined window (150), then the estimate is updated based on the length of time between the beginning of the refractory period (determined either by an applied electrical pulse of the Q-wave of an EGM signal) and the time at which activation occurred. In other examples, IMD 16 continues to probe during cardiac refractory periods during which a phrenic nerve stimulating pulse is not applied regardless of whether the previous pulse resulted in a determination of a new estimate for the cardiac refractory period. In such examples, the estimated length of the cardiac refractory period used in applying the next phrenic nerve stimulating pulse may be based on an average of the lengths of refractory periods determined since the previous stimulation. For example, the length of a first stimulation waveform for phrenic nerve electrical stimulation may be based on a first determination of cardiac refractory period length. The length of the second phrenic nerve stimulation pulse may be determined based on a second determination of cardiac refractory period length. In some examples the second determination of cardiac refractory period length may be based on the lengths of the refractory period between the first and second applications of stimulation.

In various examples, a time window may be used to determine whether an indication of activation in response to probing stimulation confirms the estimated length of cardiac refractory period. The actual time of activation in response to the probing stimulation may not be an adequate indication of the end of the relative refractory period. The ability for a cardiac cell to respond to electrical stimulation changes throughout the refractory period. If the initial probing stimulation intensity is too high, then the cardiac tissue may respond prior to the end of the relative refractory period. However, if the probing stimulation intensity is too low, then the cardiac tissue may not respond at all. Accordingly, it may be useful in some examples to modify one or both of the estimated refractory period and the probing stimulation intensity to determine whether the activation is representative of the end of the relative refractory period. In some examples, not shown in FIG. 8, IMD 16 first determines whether any activation occurred during a preset window surrounding the estimated refractory period. Then, IMD 16 proceeds to determine whether activation occurred, before, after, or not at all.

In some examples, the amount of stimulation needed to activate a cardiac tissue cell near the end of the relative refractory period may be known. In such examples, the time of response may be used in conjunction with a known beginning to the cardiac refractory period to determine the cardiac refractory period length.

In other examples, it may be desirable to determine the end of the absolute refractory period. In such examples, the simulation strength may be set at a higher initial level for the probing stimulation. The timing of a detected response to the probing stimulation may be used as an outer bound to the absolute refractory period. In the next application of probing stimulation, the stimulation level may be increased to see if early activation may be achieved. The intensity of the probing stimulation level may be increased for each subsequent refractory period, until the time from the beginning of depolarization to the activation point does not change.

Figure 9:
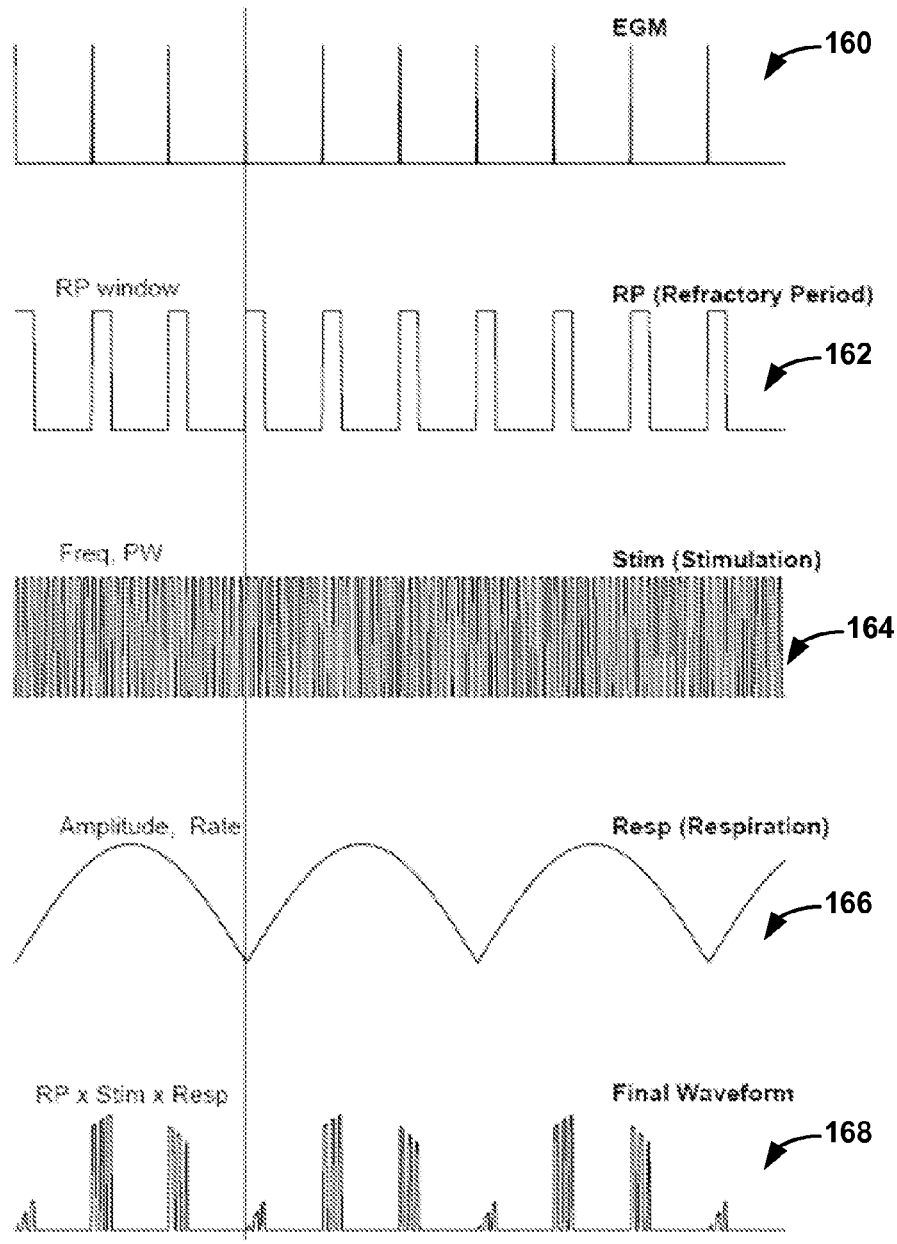
FIG. 9 is a timing diagram illustrating an example method for determining a phrenic nerve stimulation waveform.

FIG. 9 illustrates an example determination of a stimulation waveform consistent with the examples in FIGS. 5-7, but illustrating modulation of a phrenic nerve stimulation waveform according to a refractory period length and a desired respiration waveform. In this example, the timing of the refractory period is used to gate the phrenic nerve stimulation waveform, e.g., to provide a burst of phrenic nerve stimulation pulses within an estimated refractory period length following detection of a depolarization. The respiration waveform is then used to modulate the amplitude of each burst of phrenic nerve stimulation pulses, e.g., such that the phrenic nerve stimulation emulates an intensity of normal respiration over a respiration cycle. Although modulation according to a respiration waveform is shown in FIG. 9 for purposes of illustration, the phrenic nerve stimulation may not be modulated and may have a substantially constant amplitude or an amplitude that is adjusted according to a predetermined function unrelated to a respiration waveform.

Continuous phrenic nerve stimulation 164 may also stimulate cardiac tissue if applied outside the cardiac refractory period 162. Therefore, phrenic nerve stimulation may only be applied during the cardiac refractory period. The duration of the cardiac refractory period is estimated using techniques previously described.

Waveform 160 shows an example EGM signal detected by IMD 16. In some examples, the EGM signal is detected by sensing module 76. Waveform 162 is an example of an electrical signal including the length of each refractory period for a number of heart beats. As shown in FIG. 8, the beginning of the refractory period is approximately the occurrence of the R-wave of the EGM signal. In some examples, the refractory period window of waveform 162 starts at the application of a cardiac stimulating pulse, for example, and lasts for approximately 200 ms. The window is adjustable based on the estimated length of the cardiac refractory period. The refractory period waveform 162 may be generated by processor 70, for example. In some examples, the refractory period windows of waveform 162 begin at a detected depolarization and have a duration equal to the current estimated refractory period length.

Stimulation waveform 164 shows an example of a phrenic nerve stimulation waveform. In some examples, the stimulation waveform comprises a train of pulses having an amplitude of approximately 1 to 10 volts. In some examples the amplitude is approximately 1 volt peak to peak (Vpp). In various examples, the width of the pulses may range from approximately 0.1 to 2 ms, and be delivered at a pulse rate, i.e., frequency, ranging from approximately 5 to 200 Hz. In some examples the pulse width is be between approximately 0.1 and 1 ms, and be delivered at a pulse rate ranging from approximately 10 to 100 Hz. In some examples, the pulses are delivered at a frequency of approximately 30 to 60 Hz, and in some examples, the pulse frequency may be approximately 40 to 50 Hz. The shape of the stimulation waveform 164 may be determined by processor 70.

Respiration waveform 166 has a frequency corresponding to the desired breathing frequency resulting from the application of phrenic nerve stimulation. As shown in respiration waveform 166, the modulation of the amplitude of phrenic nerve stimulation may provide a more natural breathing pattern. In some examples, the respiration waveform 166 has a half sine shape. The amplitude of the respiration waveform may range from approximately 0 to 10V and in various examples may include between approximately 5 and 30 respiration cycles a minute. The shape of the respiration waveform 166 may be determined by processor 70. In some examples, processor 70 uses information from EGM waveform 140 in determining the shape of respiration waveform 166.

The final phrenic nerve stimulation waveform 168 results from applying pulse train 164 during "on" periods corresponding to refractory periods determined by waveform 162, and modulating the amplitude of the resulting pulse bursts by the respiration waveform 166 to produce phrenic nerve stimulation bursts having varying intensities over a series of refractory periods to emulate the varying respiration force of the patient. Hence, waveform 168 represents an example of phrenic nerve stimulation that may be applied by IMD 16 to at least one of phrenic nerves 36 and 38 in an example in which the intensity of the phrenic nerve stimulation varies over a series of refractory periods. In other examples, the stimulation waveform 168 may have an intensity that is the same over a series of refractory periods, or varies according to some predetermined function other than respiration waveform 166.

Phrenic nerve stimulation is shown in FIG. 9 as being applied in each refractory period for purposes of illustration. However, phrenic nerve stimulation may be applied over a plurality of refractory periods and then turned off for a plurality of refractory periods, consistent with a desired respiratory rate versus the cardiac rate of the patient. Estimation of the length of the refractory period may be performed, e.g., using probing stimulation, within refractory periods in which phrenic nerve stimulation is not delivered.

For an example in which stimulation is modulated according to a desired respiratory waveform, such as waveform 166, processor 70 or signal generator 74 may include a gate that stops signal generator 74 from applying stimulation pulses below a certain level. For example, the threshold may be set at a level where the stimulation does not trigger the diaphragm to a level that results in inspiration. This may be used in order to save the battery life of IMD 16.

Figure 10:
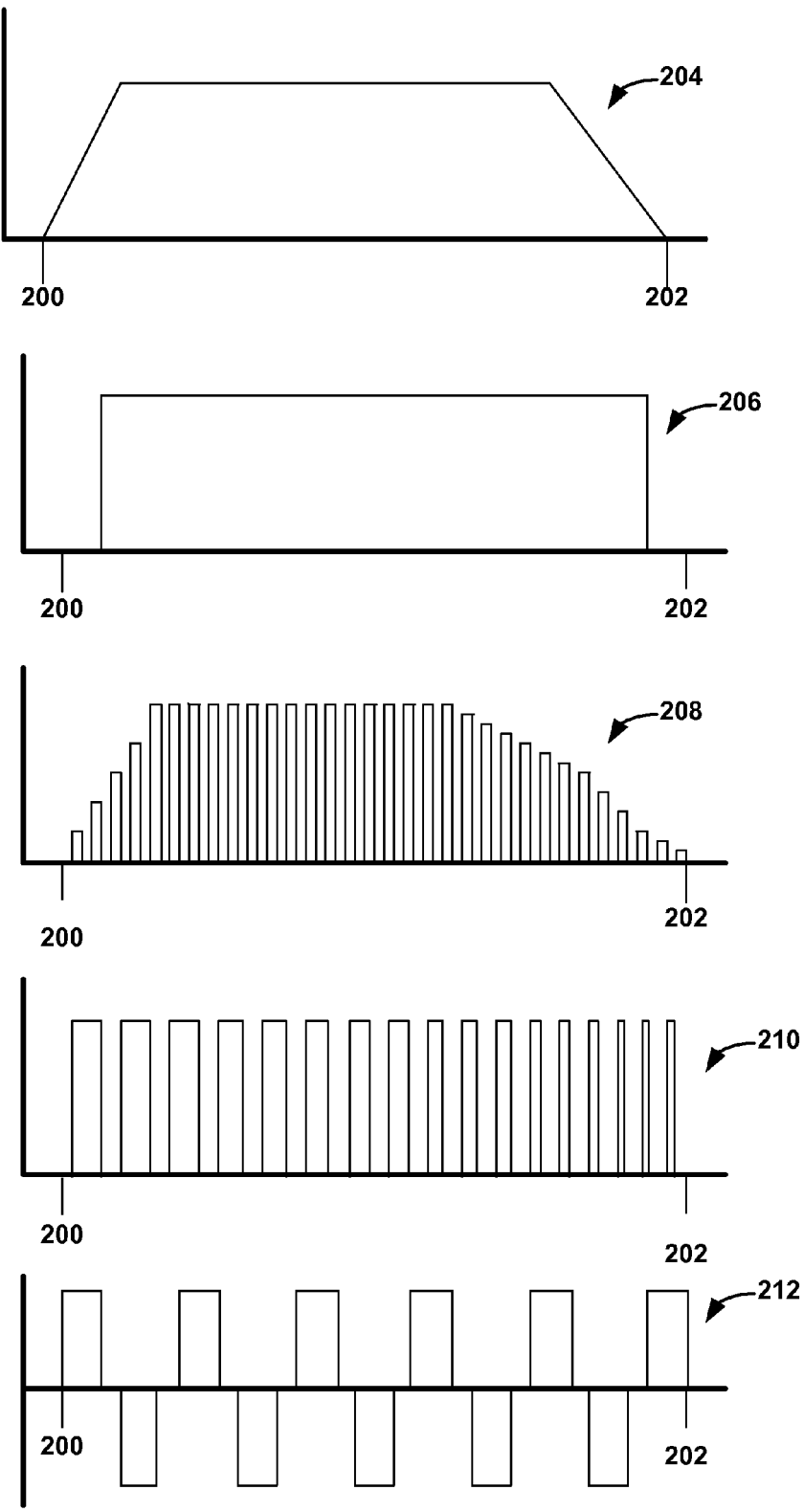
FIG. 10 is a timing diagram illustrating example waveforms for phrenic nerve stimulation.

FIG. 10 illustrates example waveforms for phrenic nerve stimulation that may be used in connection with the examples in FIGS. 5-8. For each waveform, 204, 206, 208, 210, and 212, the beginning (200) of the cardiac refractory period and the end (202) of the refractory period are shown. In some examples, the end of the refractory period (202) may correspond to the estimated length of the refractory period extending from the start of the refractory period, e.g., as determined by detection of an excitation point, an R-T interval or a predetermined time interval. In various examples, one of the waveforms 204, 206, 208 or 210 is applied via electrodes of IMD 16 to at least one of phrenic nerves 36 and 38. In some examples waveforms 204, 206, 208, 210 and 212 may have an amplitude of between approximately 1-10V. In some examples, the amplitude may between approximately 0 and 4V, and in some examples the waveform may have a peak amplitude between approximately 1 and 2 V. In some examples, the pulse width may be between 0.1 and 1 ms. In some examples, the pulse width may be between approximately 0.1 and 0.2 ms. In some pulses may be applied at a frequency of between approximately 10-100 Hz. In some examples the frequency may be between approximately 30-60 Hz, and in some examples the frequency may be between approximately 40-50 Hz.

Other waveforms, not depicted may also be applied. As an illustration, the phrenic nerve stimulation is applied during every sixth heart beat (i.e., every sixth refractory period), for example, in order to provide a breathing rate of approximately 10 breaths per minute. In other examples, phrenic nerve stimulation may be applied in a number of successive cardiac refractory periods. For example, in order to prolong inspiration, stimulation may be provided over multiple cardiac refractory periods. However, the phrenic nerve needs a period of relaxation in order to allow for expiration.

In other examples, the number of heart beats, and refractory periods, between applications of phrenic nerve stimulation is determined by dividing the heart rate by the desired respiratory rate. In some examples, processor 70 updates the number of refractory periods between stimulation based on changes in activity level detected by activity monitor 84. For example, if the activity level indicates the patient is exercising, the desired respiratory rate may go up. The heart rate may go up as well. However, as respiratory rate and heart rate may not always increase at the same rate, the number of refractory periods between stimulations may need to be recalculated.

Waveform 204 represents a continuous waveform. However, any of the waveforms may be continuous or pulsed, as shown in FIG. 10. In waveform 204, the amplitude of the stimulation intensity increases gradually at the beginning of the refractory period according to a ramp function, and decreases gradually towards the end of the refractory period according to a ramp function. Gradually increasing and decreasing stimulation intensity near the bounds of the refractory period may provide additional assurance that the phrenic nerve stimulation will not cause the cardiac muscle to depolarize, causing an unintended heart beat or other undesirable cardiac activation. For example, the increase at the beginning of the waveform ensures that the maximum amplitude of the electrical stimulation occurs after the refractory period has begun. Similarly, the down slope at the end of stimulation waveform 204 may allow for stimulation of the phrenic nerve for a longer period of time without causing an action potential in the cardiac tissue surrounding the electrode, i.e., in the relative refractory period. The absolute values of the up slope and down slope may be the same or different. The amplitude in the down slope may be selected to be below a level sufficient to cause undesirable cardiac activation in the relative refractory period. As discussed above, during the relative refractory period, the amount of stimulation needed to trigger an action potential decrease until it returns to the normal threshold level. By decreasing the intensity of the stimulation as the end of the estimated refractory period nears, e.g., by decreasing the voltage or current amplitude as shown in FIG. 10, the phrenic nerve stimulation is less likely to provide enough stimulation to surrounding cardiac tissue to result in an action potential.

Phrenic nerve stimulation waveform 206 includes margins of time between the beginning of the refractory period and the start of the phrenic nerve stimulation, and between the end of the phrenic nerve stimulation and the end of the estimated refractory period. The inclusion of one or more of the time margins reduces the likelihood of activating the cardiac muscle tissue surrounding the electrodes, providing stimulation to at least one of phrenic nerves 36 and 38. For example, during the margins, stimulation may not be applied even though the margins reside in the refractory period. The margins buffer the phrenic nerve stimulation with respect to the start and end bounds of the estimated refractory period to reduce the risk of undesirable cardiac stimulation. In other examples, the stimulation may be applied at a reduced amplitude at the beginning or end of the refractory period to reduce the likelihood of activating the cardiac tissue. In some examples, a margin of time may only be used at the end of the refractory period, wherein the relative refractory period may increase the risk of undesirable cardiac activation. Hence, a margin may include a period of reduced amplitude stimulation, particularly in instances where stimulation is being applied during the relative refractory period. In some examples, the margin employed may depend on the method used to estimate the refractory period. In some examples, the less accurate the refractory period estimation, the greater the safety margin used. For example, if the cardiac refractory period is estimated based on a population average, then a greater safety margin is used than if the cardiac refractory period is estimated based on the Q-T interval.

Stimulation waveform 208 is another example of a phrenic nerve stimulation waveform. In stimulation waveform 208, pulses of varying amplitudes, but the same pulse width and pulse rate, are applied. As discussed with respect to waveform 204, the increase and decrease in stimulation amplitude may help ensure that the phrenic nerve stimulation does not trigger an unwanted heart beat, while still allowing for application of stimulation to the phrenic nerve during approximately the entire refractory period. The longer the application of stimulation, the less likely unwanted breathing patterns such as hiccups are to occur. In addition, the longer the stimulation, the deeper and longer the inspiration the stimulation is able to achieve Stimulation waveform 210 is another example of a phrenic nerve stimulation waveform comprising a number of pulses. In waveform 210, the amplitude of each pulse is consistent. However, the length of time the pulse is applied to at least one of phrenic nerves 36 and 38 decreases throughout the refractory period. In particular, the pulse width of the pulses varies from longer at near the start of the estimated refractory period to shorter toward the end of the refractory period, such that intensity decreases toward the end of the refractory period.

Stimulation waveform 212 is another example of a phrenic nerve stimulation waveform comprising a number of pulses. In waveform 212 the pulses applied to one or both of phrenic nerves 36 and 38 are bipolar pulses. Again, the start of the refractory period may be estimated based on delivery of a pacing pulse or detection of a paced or intrinsic depolarization in the EGM signal. The end of the refractory period may be estimated based on an excitation point at which probing stimulation produces cardiac excitation, based on a predetermined interval of time following the start of the refractory period, or based on a detected R-T interval in the EGM signal. Upon estimation of the refractory period length, various waveforms such as those shown in FIG. 10 may be delivered within the estimated length of the refractory period following the detected start of the refractory period.

Figure 11:
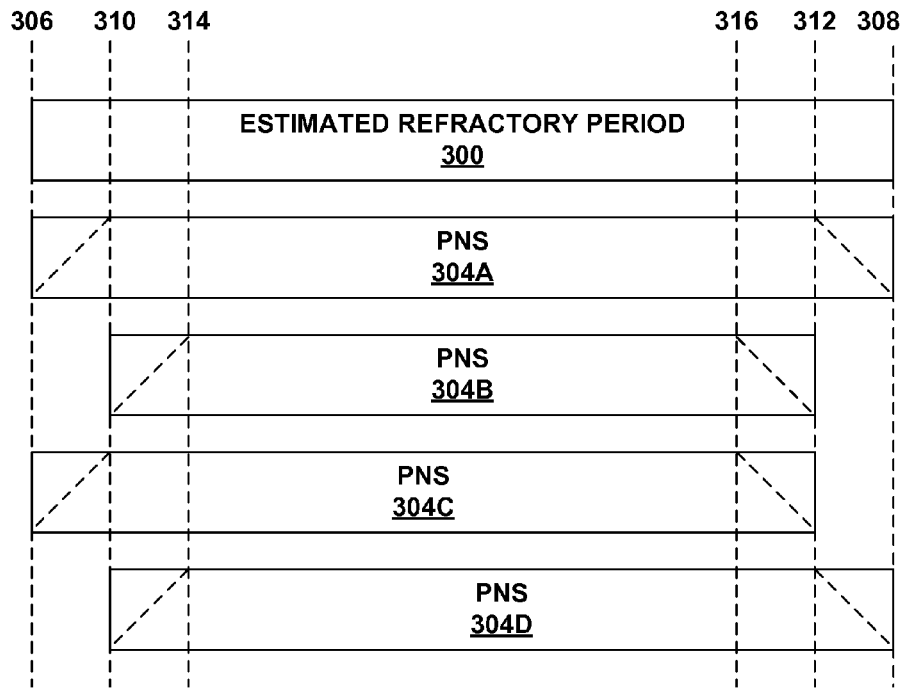
FIG. 11 is a timing diagram illustrating examples of selective adjustment of length and intensity of phrenic nerve stimulation relative to an estimated length of a refractory period.

FIG. 11 is a timing diagram illustrating examples of selective adjustment of length and intensity of phrenic nerve stimulation relative to an estimated length of a refractory period. The length of estimated refractory period 300 may be estimated based on the method described with respect to FIG. 8, for example. In other examples the length of estimated refractory period 300 may be estimated based on an EGM signal. Estimated refractory period has a start 306 and an end 308. In some examples, start 306 is based on the application of a pacing stimulation pulse by signal generator 74, for example. In some examples, start 306 is based on the detection by sensing module 76, for example. In some examples start 306 is based on a detected intrinsic depolarization. In some examples, the end 308 of estimated refractory period 300 is at a predetermined interval after start 306. In other examples, the end 308 occurs at a time after the start 306 based on the estimate of the length of the refractory period. In some examples, the length of the refractory period may be estimated based on pacing pulses. In some examples, the length of the refractory period may be estimated based on information from an EGM signal. In some examples, the location of end 308 may be based on the occurrence of a T-wave as detected by sensing module 76, for example.

FIG. 11 also illustrates the timing of a variety of phrenic nerve stimulation waveforms 304A, 304B, 304C and 304D. PNS 304A includes an optional ramp period from start 306 to a first margin 310 and an optional ramp period from a second margin 312 to the end 308 of estimated refractory period 300. PNS 304B does not start until time margin 310 and has an optional ramp between first margin 310 and margin 314. PNS 304B also includes an optimal ramp between margin 316 and second margin 312. PNS 304B ends at second margin 312. PNS 304C includes an optional ramp period between start 306 and first margin 310 and an optional ramp period between margin 316 and second margin 312. PNS 304C end at second margin 312. PNS 304D starts at first margin 312, and has an optional ramp between first margin 310 and margin 314. PNS 304D ends at end 308 and includes and optional ramp between second margin 312 and end 308. In some examples, the ramps between 306 and 310 and 310 and 314 have different slopes than the ramps between 316 and 312 and 312 and 308. In some examples, the intensity of the PNS waveform ramps up at the beginning of the PNS. In some examples, the intensity of the PNS waveform ramps down towards the end of the PNS.

Figure 12:
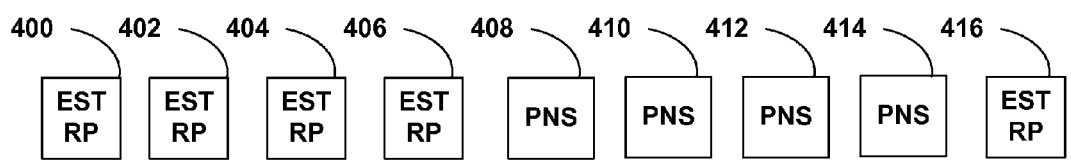
FIG. 12 is a timing diagram illustrating examples of estimating a refractory period length and delivering phrenic nerve stimulation based on the estimated refractory period length.

FIG. 12 is a timing diagram illustrating examples of estimating a refractory period length and delivering phrenic nerve stimulation based on the estimated refractory period length. As shown in FIG. 12, the both the estimation of refractory period length and application of phrenic nerve stimulation may occur over a plurality of cardiac cycles. In some examples, the estimation of refractory period length is resumed after the application of phrenic nerve stimulation in anticipation of the next application of phrenic nerve stimulation. During refractory period 400, 402, 404, 406 and 408, the length of the refractory period is estimated. In some examples, IMD 16 estimates the length of the refractory period using probing stimulation as described with respect to FIG. 8. In some examples, the length of the refractory period is estimated based on information from an EGM signal. In some examples, the length of the refractory periods 400, 402, 404, 406 and 408 are estimated independent of one another. In some examples the individual estimations are averaged for use during phrenic nerve stimulation. In other examples, the length of each refractory period uses information collected during the estimation of the previous refractory period. For example, the estimation of the length of refractory period 404 may rely on information collected during both refractory period 400 and refractory period 402. During refractory periods 410, 412 and 414 phrenic nerve stimulation is applied. In some examples, the duration of the phrenic nerve stimulation is based on an estimated refractory period length. In some examples the phrenic nerve stimulation length is based on an average of estimated refractory period lengths preceding the stimulation. In some examples, the length of PNS during refractory periods 408, 410, 412, and 414 is the same, and is based on the estimated length of refractory period 406. In some examples, PNs during refractory period 408, 410, 412 and 414 result in a single inspiration by patient 14. In some examples, after the PNS during refractory period 414, IMD begins estimating the length of the refractory period again in refractory period 416. In some examples, the estimation of refractory period 416 builds on the estimation of refractory period 406.

In various examples, phrenic nerve stimulation is applied every Nth cardiac cycle (as depicted, every fifth cardiac cycle) for one or more cycles (as depicted, for four cycle). This is possible because the frequency of respiration is lower than cardiac frequency (heart rate). In addition, any period of inspiration must be followed by a period of expiration.

The techniques described in this disclosure may be implemented, at least in part, in hardware, software, firmware or any combination thereof. For example, various aspects of the techniques may be implemented within one or more microprocessors, digital signal processors (DSPs), application specific integrated circuits (ASICs), field programmable gate arrays (FPGAs), or any other equivalent integrated or discrete logic circuitry, as well as any combinations of such components, embodied in programmers, such as physician or patient programmers, stimulators, or other devices. The terms "processor," "processing circuitry," "controller" or "control module" may generally refer to any of the foregoing logic circuitry, alone or in combination with other logic circuitry, or any other equivalent circuitry, and alone or in combination with other digital or analog circuitry.

For aspects implemented in software, at least some of the functionality ascribed to the systems and devices described in this disclosure may be embodied as instructions on a computer-readable storage medium such as random access memory (RAM), read-only memory (ROM), non-volatile random access memory (NVRAM), electrically erasable programmable read-only memory (EEPROM), FLASH memory, magnetic media, optical media, or the like. The instructions may be executed to support one or more aspects of the functionality described in this disclosure.

Various examples have been described. These and other examples are within the scope of the following claims.

The invention claimed is:

1. A method comprising:
   estimating a length of a cardiac refractory period; and
   selectively adjusting a length of phrenic nerve electrical stimulation to be delivered to a patient based at least in part on the estimated length of the cardiac refractory period; and
   wherein estimating a length of the cardiac refractory period comprises estimating the length based at least in part on a cardiac signal of the patient; and,
   further comprising monitoring the cardiac signal; wherein:
   monitoring a cardiac signal comprises monitoring the cardiac signal over a plurality of cardiac cycles;
   estimating a length of a cardiac refractory period comprises updating the estimated length of the cardiac refractory period based at least in part on the cardiac signal monitored over the plurality of cardiac cycles; and
   selectively adjusting a length of phrenic nerve electrical stimulation comprises selectively adjusting the length of the phrenic nerve electrical stimulation based on the updated estimated length.

2. The method of claim 1, further comprising selectively adjusting the length of the phrenic nerve electrical stimulation in proportion with the estimated length of the cardiac refractory period.

3. The method of claim 1, further comprising delivering the phrenic nerve electrical stimulation to the patient for a period of time approximately equal to the estimated length of the refractory period minus a predetermined time margin.

4. The method of claim 1, further comprising estimating the length of the refractory period based on detection of cardiac excitation in response to delivery of probing stimulation during one or more refractory periods.

5. The method of claim 1, wherein the phrenic nerve electrical stimulation has a waveform comprising greater stimulation intensity at a beginning of the waveform than at an end of the waveform.

6. The method of claim 1, wherein the phrenic nerve electrical stimulation has a waveform comprising a plurality of pulses.

7. The method of claim 1, further comprising delivering the phrenic nerve electrical stimulation at a predetermined length of time after a cardiac stimulation pulse.

8. The method of claim 1, wherein the cardiac signal is an electrogram (EGM) signal, the method further comprising delivering the phrenic nerve electrical stimulation after the detection of an R-wave of the EGM signal.

9. The method of claim 1, wherein the phrenic nerve electrical stimulation waveform is selected to induce respiration to alleviate sleep apnea.

10. The method of claim 1, further comprising delivering the phrenic nerve electrical stimulation for approximately the entire estimated length of the refractory period.

11. The method of claim 1, wherein a beginning of the cardiac refractory period is a result of a pacing pulse.

12. A method comprising:
    estimating a length of a cardiac refractory period; and
    selectively adjusting a length of phrenic nerve electrical stimulation to be delivered to a patient based at least in part on the estimated length of the cardiac refractory period;
    wherein selectively adjusting a length of phrenic nerve electrical stimulation comprises:
    determining a first length of the phrenic nerve electrical stimulation based on a first estimated length of the refractory period;
    applying the phrenic nerve electrical stimulation with the first length during a first refractory period;
    monitoring one or more refractory periods following the first refractory period, and based on the one or more monitored refractory periods, estimating a second length of the refractory period;
    determining a second length of the phrenic nerve electrical stimulation based on the second estimated length of the refractory period; and
    applying the phrenic nerve stimulation with the second length during a subsequent refractory period.

13. A device comprising:
    a processor configured to estimate a length of a cardiac refractory period and selectively adjust a length of phrenic nerve electrical stimulation to be delivered to a patient based at least in part on the estimated length of the cardiac refractory period; and
    wherein the processor is further configured to estimate the length of the cardiac refractory period based at least in part on a cardiac signal of a patient; and
    further comprising monitoring a cardiac signal; wherein:
    the sensor is configured to monitor the cardiac signal over a plurality of cardiac cycles; and
    the processor if further configured to
    update the estimated length of the cardiac refractory period based at least in part on the cardiac signal monitored over the plurality of cardiac cycles, and
    selectively adjust the length of phrenic nerve electrical stimulation based on the updated estimated length.

14. The device of claim 13, wherein the processor is further configured to selectively adjust the length of the phrenic nerve stimulation in proportion with the estimated length of the refractory period.

15. The device of claim 13, further comprising a signal generator configured to deliver the phrenic nerve electrical stimulation to the patient for a period of time approximately equal to the estimated length of the refractory period minus a predetermined time margin.

16. The device of claim 13, wherein the processor is further configured to estimate the length of the refractory period based on detection of cardiac excitation in response to delivery of probing stimulation during one or more refractory periods.

17. The device of claim 13, further including a signal generator configured to provide the phrenic nerve electrical stimulation having a waveform comprising greater stimulation intensity at a beginning of the waveform than at an end of the waveform.

18. The device of claim 13, further including a signal generator configured to provide the phrenic nerve electrical stimulation having a waveform comprising a plurality of pulses.

19. The device of claim 13, further including a signal generator configured to deliver the phrenic nerve electrical stimulation a predetermined length of time after a cardiac stimulation pulse.

20. The device of claim 13, wherein the cardiac signal is an electrogram (EGM) signal and further including a signal generator configured to deliver delivery the phrenic nerve electrical stimulation after the detection of an R-wave of the EGM signal.

21. The device of claim 13, wherein the processor is further configured to select a phrenic nerve electrical stimulation waveform configured to induce respiration to alleviate sleep apnea.

22. The device of claim 13, further comprising a signal generator configured to deliver the phrenic nerve electrical stimulation for approximately the entire estimated refractory period.

23. A device comprising:
a processor configured to estimate a length of a cardiac refractory period and selectively adjust a length of phrenic nerve electrical stimulation to be delivered to a patient based at least in part on the estimated length of the cardiac refractory period; and
wherein the processor is further configured to:
determine a first length of the phrenic nerve electrical stimulation based on a first estimated length of the refractory period;
apply the phrenic nerve electrical stimulation with the first length during a first refractory period;
monitor one or more refractory periods following the first refractory period, and based on the one or more monitored refractory periods, estimating a second length of the refractory period;
determine a second length of phrenic nerve electrical stimulation based on the second estimated length of the refractory period; and
apply the phrenic nerve stimulation with the second length during a subsequent refractory period.

24. A device comprising:
means for estimating a length of a cardiac refractory period; and
means for selectively adjusting a length of phrenic nerve electrical stimulation to be delivered to the patient based at least in part on the estimated length of the cardiac refractory period; wherein
the means for monitoring monitors the cardiac signal over a plurality of cardiac cycles;
the means for estimating updates the estimated length of the cardiac refractory period at a plurality of times based at least in part on the cardiac signal monitored over the plurality of cardiac cycles; and
the means for selectively adjusting selecting adjusts the length of the phrenic nerve electrical stimulation based on the updated estimated length.

25. A device comprising:
means for estimating a length of a cardiac refractory period; and
means for selectively adjusting a length of phrenic nerve electrical stimulation to be delivered to the patient based at least in part on the estimated length of the cardiac refractory period; wherein the means for selectively adjusting comprises
means for determining a first length of the phrenic nerve electrical stimulation based on a first estimated length of the refractory period;
means for applying the phrenic nerve electrical stimulation with the first length during a first refractory period;
means for monitoring one or more refractory periods following the first refractory period, and based on the one or more monitored refractory periods, estimating a second length of the refractory period;
means for determining a second length of the phrenic nerve electrical stimulation based on the second estimated length of the refractory period; and
means for applying the phrenic nerve stimulation with the second length during a subsequent refractory period.

26. The device of claim 25, further comprising means for selectively adjusting the phrenic nerve electrical stimulation in proportion with the estimated length of the cardiac refractory period.

27. The device of claim 25, further comprising means for delivering the phrenic nerve electrical stimulation to the patient for a period of time approximately equal to the estimated length of the refractory period minus a predetermined time margin.

28. The device of claim 25, further comprising means for estimating the length of the refractory period based on detection of cardiac excitation in response to deliver of probing stimulation during one or more refractory periods.

* * * * *